(12) United States Patent
Ubasawa et al.

(10) Patent No.: US 6,194,398 B1
(45) Date of Patent: Feb. 27, 2001

(54) PHOSPHONATE NUCLEOTIDE COMPOUND

(75) Inventors: Masaru Ubasawa; Kouichi Sekiya; Hideaki Takashima; Naoko Ueda; Satoshi Yuasa; Naohiro Kamiya, all of Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/242,111

(22) PCT Filed: Aug. 12, 1997

(86) PCT No.: PCT/JP97/02819

§ 371 Date: Jun. 17, 1999

§ 102(e) Date: Jun. 17, 1999

(87) PCT Pub. No.: WO98/06726

PCT Pub. Date: Feb. 19, 1998

(30) Foreign Application Priority Data

Aug. 13, 1996 (JP) .................................................. 8-213691

(51) Int. Cl.[7] ..................... C07D 473/24; C07D 487/04; A61K 31/52; A61K 31/519; A61P 31/20
(52) U.S. Cl. .............................................. 514/81; 544/244
(58) Field of Search ................................ 544/244; 514/81

(56) References Cited

FOREIGN PATENT DOCUMENTS

| 0 468 866 A1 | 1/1992 | (EP) . |
| 0 632 048 A1 | 1/1995 | (EP) . |
| 0 785 208 A1 | 7/1997 | (EP) . |

OTHER PUBLICATIONS

Holy et al, Nucleosides & Nucleotides, 7, 1988, 667–70.*
Holy et alColl. Czech. Chem. Comm., 60, 1995, 1390–1409.*

Starrett et al, Antiviral Res., 19, 1992, 267–273.*

* cited by examiner

Primary Examiner—Mark L. Berch
Assistant Examiner—Thomas McKenzie
(74) Attorney, Agent, or Firm—Sughrue, Mion, Zinn, Macpeak & Seas, PLLC

(57) ABSTRACT

A phosphonate nucleotide compound represented by formula (I):

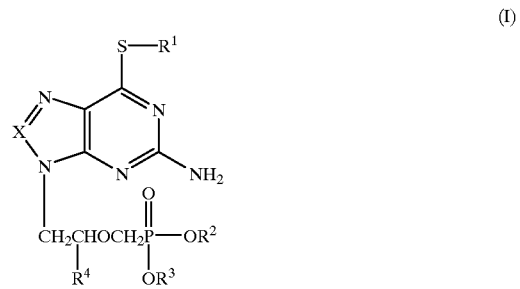

(wherein $R^1$ is a $C_1$–$C_6$ alkyl group or the like, $R^2$ is a hydrogen atom, a $C_1$–$C_4$ alkyl group substituted by one or more halogen atoms or the like, $R^3$ is a hydrogen atom, a $C_1$–$C_4$ alkyl group substituted by one or more halogen atoms or the like, $R^4$ is a hydrogen atom, a $C_1$–$C_4$ alkyl group substituted by one or more halogen atoms and X is a carbon atom or a nitrogen atom), a salt thereof, a hydrate thereof or a solvate thereof, as well as a medicament containing the same. It is useful as an antiviral agent for human immunodeficiency virus, herpes simplex virus, hepatitis B virus or the like and as an antitumor agent.

10 Claims, No Drawings

PHOSPHONATE NUCLEOTIDE COMPOUND

CROSS-REFERENCE TO RELATED APPLICATION

This application is a 371 of PCT/JP97/02819 Aug. 12, 1997.

TECHNICAL FIELD

This invention relates to novel phosphonate nucleotide compounds, more particularly, it relates to novel phosphonate nucleotide compounds which have antiviral activity and are useful as medicaments, their salts, their hydrates or their solvates.

BACKGROUND ART

Infectious viral diseases are recognized as an important medical problem and, with the aim of treating such diseases, attempts have been made to develop a drug which has antiviral activity but has no activity to inhibit growth of normal cell lines. For example, extensive studies have been conducted on phosphonate nucleotides as selective antiviral agents. Illustratively, it has been reported that 9-(2-phosphonylmethoxy)ethyladenine (PMEA), 9-(2-phosphonylmethoxy)ethyl-2,6-diaminopurine (PMDAP) and the like compounds are effective against herpes simplex virus type 1 and type 2 (HSV-1 and HSV-2), human immunodeficiency virus (HIV) and human hepatitis B virus (HBV) (Yokota et al., *Antimicrob. Agents Chemother.*, 35, 394 (1991); Votruba et al., *Mol. Pharmacol.*, 3, 524 (1987)).

However, these known phosphonate nucleotides have a problem in terms of safety such as a possibility of causing toxicity and mutagenicity, typically including bone marrow cell growth inhibition, in the living body (*Antiviral Research*, 16, 77 (1991)), and, since these compounds do not have oral absorption ability (De Clercq et al., *Antimicrob. Agents Chemother.*, 33, 185 (1989)), their route of administration is limited to intravenous injection, intramuscular injection and the like parenteral administration in order to obtain enough blood levels for exerting their effects. Since the treatment by parenteral administration is difficult to apply to outpatients, such a method is not suitable for the treatment of AIDS, hepatitis B and the like diseases which require long-term therapy.

On the other hand, the inventors of the present invention have previously found that specified ester derivatives of a phosphonate nucleotide show high oral absorption ability (EP 632048), but they have not been put into practical use yet.

DISCLOSURE OF THE INVENTION

The present invention contemplates providing novel compounds which show high antiviral activity and higher safety for the living body in comparison with the compounds so far proposed, simultaneously having high oral absorption ability.

The present invention relates to phosphonate nucleotide compounds represented by formula (I):

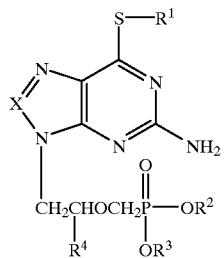

(I)

(in the above formula (I), $R^1$ represents a $C_1$–$C_6$ alkyl group or a $C_7$–$C_{10}$ aralkyl group, each of $R^2$ and $R^3$ independently represents a hydrogen atom (with the proviso that $R^2$ and $R^3$ are not hydrogen atoms at the same time), a $C_1$–$C_{22}$ alkyl group, an acyloxymethyl group, an acylthioethyl group or an ethyl group substituted by one or more halogen atoms, $R^4$ represents a hydrogen atom, a $C_1$–$C_4$ alkyl group, a $C_1$–$C_4$ hydroxyalkyl group or a $C_1$–$C_4$ alkyl group substituted by one or more halogen atoms and X represents a carbon atom or a nitrogen atom), a salt thereof, a hydrate thereof or a solvate thereof, as well as a pharmaceutical composition and an antiviral agent each of which comprises these compounds.

BEST MODE OF CARRYING OUT THE INVENTION

The following describes the present invention in detail.

In the phosphonate nucleotide derivatives represented by the just described formula (I), examples of the $C_1$–C6 alkyl group defined by $R^1$ include methyl, ethyl, n-propyl, isopropyl, n-butyl, isobutyl, sec-butyl, tert-butyl, n-pentyl, n-hexyl and the like groups.

Examples of the $C_7$–$C_{10}$ aralkyl group defined by $R^1$ include benzyl, phenetyl, phenylpropyl, phenylbutyl and the like groups.

According to the present invention, preferred is a compound in which $R^1$ is the just described $C_1$–$C_6$ alkyl group or benzyl group, more preferably a $C_1$–$C_6$ alkyl group.

Examples of the $C_1$–$C_{22}$ alkyl group defined by $R^2$ and $R^3$ include methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl and the like groups.

Examples of the acyloxymethyl group of $R^2$ and $R^3$ include acetyloxymethyl, propionyloxymethyl, butyryloxymethyl, isobutyryloxymethyl, valeryloxymethyl, isovaleryloxymethyl, pivaloyloxymethyl and the like groups.

Examples of the acylthioethyl group of $R^2$ and $R^3$ include acetylthioethyl, propionylthioethyl, butyrylthioethyl, isobutyrylthioethyl, valerylthioethyl, isovalerylthioethyl, pivaloylthioethyl and the like groups.

With regard to the ethyl group of $R^2$ and $R^3$ substituted by one or more halogen atoms, examples of the halogen atom include fluorine, chlorine, bromine, iodine and the like atoms, and examples of the ethyl group substituted by one or more halogen atoms include 1-fluoroethyl, 2-fluoroethyl, 1-chloroethyl, 2-chloroethyl, 2-bromoethyl, 2,2-difluoroethyl, 2,2-dichloroethyl, 2,2-dibromoethy, 2,2,2-trifluoroethyl, 2,2,2-trichloroethyl, 2,2,2-tribromoethyl and the like groups, wherein it is particularly desirable that the 2-position of ethyl group is substituted, and fluorine atom is desirable as the halogen atom.

It is desirable that at least one of $R^2$ and $R^3$ is an ethyl group substituted by one or more halogen atoms, particularly 2,2,2-trifluoroethyl group.

Examples of the $C_1$–$C_4$ alkyl group of R4 include methyl, ethyl, n-propyl, isopropyl, n-butyl, isobutyl, sec-butyl, tert-butyl and the like groups.

Examples of the $C_1$–$C_4$ hydroxyalkyl group of $R^4$ include hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl and the like groups.

With regard to the $C_1$–$C_4$ alkyl group of $R^4$ substituted by one or more halogen atoms, examples of the halogen atom include fluorine, chlorine and the like atoms, examples of the $C_1$–$C_4$ alkyl group include methyl, ethyl, n-propyl, isopropyl, n-butyl, isobutyl, sec-butyl, tert-butyl and the like groups, and examples of the $C_1$–$C_4$ alkyl group substituted by one or more halogen atoms include fluoromethyl, difluoromethyl, trifluoromethyl, fluoroethyl, chloroethyl, fluoropropyl, chloropropyl, fluorobutyl, chlorobutyl and the like groups.

According to the present invention, a compound in which $R^4$ is hydrogen atom is desirable.

Also, according to the present invention, a compound in which X is carbon atom is desirable.

The phosphonate nucleotide compound of the present invention represented by the aforementioned formula (I) can form a pharmaceutically acceptable salt. With regard to illustrative examples of such a salt, it can form lithium salt, sodium salt, potassium salt, magnesium salt, calcium salt and the like metal salts or ammonium salt, methylaimonium salt, dimethylanmonium salt, trimethylammonium salt, dicyclohexylammonium salt and the like ammonium salts when an acidic group is present, and it can form hydrochloride, hydrobromide, sulfate, nitrate, phosphate and the like mineral acid salts or methanesulfonate, benzenesulfonate, paratoluenesulfonate, acetate, propionate, tartarate, fumarate, maleate, malate, oxalate, succinate, citrate, benzoate, mandelate, cinnamate, lactate and the like organic acid salts when a basic group is present.

In addition, the phosphonate nucleotide compound of the present invention represented by the aforementioned formula (I) or salts thereof can exist in the form of hydrates or solvates, and these hydrates and solvates are also included in the present invention. Examples of the solvent capable of forming solvates include methanol, ethanol, isopropanol, acetone, ethyl acetate, methylene chloride and the like.

Illustrative examples of the compound of the present invention are shown in Table 1 below. In the table, Me means methyl group, Et means ethyl group, n-Pr means n-propyl group, i-Pr means isopropyl group, n-Bu means n-butyl group, i-Bu means isobutyl group, s-Bu means second-butyl group, t-Bu means tertiary-butyl group, n-Pen means n-pentyl group and n-Hex means n-hexyl group.

As an analog of these compounds, a compound in which the phosphonate moiety is dissociated, namely 2-amino-9-[2-(phosphonylmethoxy)ethyl]-6-alkylthiopurine, has been applied as a patent by the U.S. Department of Health and Human Service (U.S. Pat. No. 7,683,432). However, illustrative data on its antiviral action and synthesis examples and physical data of the compound are not described in said patent. According to the invention of the present application, as will be shown later in Test Example 2, when the compound of the just cited reference was compared with the compound of the present invention, it was found that the compound of the present invention has superior oral absorption ability and is accumulated in the liver in a specific fashion.

TABLE 1

| Comp. No. | $R^1$ | $R^2$ | $R^3$ | $R^4$ | X |
|---|---|---|---|---|---|
| 1 | Me | —CH$_2$CF$_3$ | —CH$_2$CF$_3$ | H | C |
| 2 | Et | —CH$_2$CF$_3$ | —CH$_2$CF$_3$ | H | C |
| 3 | n-Pr | —CH$_2$CF$_3$ | —CH$_2$CF$_3$ | H | C |
| 4 | i-Pr | —CH$_2$CF$_3$ | —CH$_2$CF$_3$ | H | C |
| 5 | n-Bu | —CH$_2$CF$_3$ | —CH$_2$CF$_3$ | H | C |
| 6 | i-Bu | —CH$_2$CF$_3$ | —CH$_2$CF$_3$ | H | C |
| 7 | s-Bu | —CH$_2$CF$_3$ | —CH$_2$CF$_3$ | H | C |
| 8 | t-Bu | —CH$_2$CF$_3$ | —CH$_2$CF$_3$ | H | C |
| 9 | n-Pen | —CH$_2$CF$_3$ | —CH$_2$CF$_3$ | H | C |
| 10 | n-Hex | —CH$_2$CF$_3$ | —CH$_2$CF$_3$ | H | C |
| 11 | Me | —CH$_2$CF$_3$ | —CH$_2$CF$_3$ | H | N |
| 12 | Et | —CH$_2$CF$_3$ | —CH$_2$CF$_3$ | H | N |
| 13 | n-Pr | —CH$_2$CF$_3$ | —CH$_2$CF$_3$ | H | N |
| 14 | i-Pr | —CH$_2$CF$_3$ | —CH$_2$CF$_3$ | H | N |
| 15 | n-Bu | —CH$_2$CF$_3$ | —CH$_2$CF$_3$ | H | N |
| 16 | i-Bu | —CH$_2$CF$_3$ | —CH$_2$CF$_3$ | H | N |
| 17 | s-Bu | —CH$_2$CF$_3$ | —CH$_2$CF$_3$ | H | N |
| 18 | t-Bu | —CH$_2$CF$_3$ | —CH$_2$CF$_3$ | H | N |
| 19 | n-Pen | —CH$_2$CF$_3$ | —CH$_2$CF$_3$ | H | N |
| 20 | n-Hex | —CH$_2$CF$_3$ | —CH$_2$CF$_3$ | H | N |
| 21 | Me | Me | —CH$_2$CF$_3$ | H | C |
| 22 | Et | Me | —CH$_2$CF$_3$ | H | C |
| 23 | n-Pr | Me | —CH$_2$CF$_3$ | H | C |
| 24 | i-Pr | Me | —CH$_2$CF$_3$ | H | C |
| 25 | n-Bu | Me | —CH$_2$CF$_3$ | H | C |
| 26 | i-Bu | Me | —CH$_2$CF$_3$ | H | C |
| 27 | s-Bu | Me | —CH$_2$CF$_3$ | H | C |
| 28 | t-Bu | Me | —CH$_2$CF$_3$ | H | C |
| 29 | n-Pen | Me | —CH$_2$CF$_3$ | H | C |
| 30 | n-Hex | Me | —CH$_2$CF$_3$ | H | C |

TABLE 1-continued

| Comp. No. | R¹ | R² | R³ | R⁴ | X |
|---|---|---|---|---|---|
| 31 | Me | Me | —CH₂CF₃ | H | N |
| 32 | Et | Me | —CH₂CF₃ | H | N |
| 33 | n-Pr | Me | —CH₂CF₃ | H | N |
| 34 | i-Pr | Me | —CH₂CF₃ | H | N |
| 35 | n-Bu | Me | —CH₂CF₃ | H | N |
| 36 | i-Bu | Me | —CH₂CF₃ | H | N |
| 37 | s-Bu | Me | —CH₂CF₃ | H | N |
| 38 | t-Bu | Me | —CH₂CF₃ | H | N |
| 39 | n-Pen | Me | —CH₂CF₃ | H | N |
| 40 | n-Hex | Me | —CH₂CF₃ | H | N |
| 41 | Me | —CH₂CF₃ | Et | H | C |
| 42 | Et | —CH₂CF₃ | Et | H | C |
| 43 | n-Pr | —CH₂CF₃ | Et | H | C |
| 44 | i-Pr | —CH₂CF₃ | Et | H | C |
| 45 | n-Bu | —CH₂CF₃ | Et | H | C |
| 46 | i-Bu | —CH₂CF₃ | Et | H | C |
| 47 | s-Bu | —CH₂CF₃ | Et | H | C |
| 48 | t-Bu | —CH₂CF₃ | Et | H | C |
| 49 | n-Pen | —CH₂CF₃ | Et | H | C |
| 50 | n-Hex | —CH₂CF₃ | Et | H | C |
| 51 | Me | —CH₂CF₃ | Et | H | N |
| 52 | Et | —CH₂CF₃ | Et | H | N |
| 53 | n-Pr | —CH₂CF₃ | Et | H | N |
| 54 | i-Pr | —CH₂CF₃ | Et | H | N |
| 55 | n-Bu | —CH₂CF₃ | Et | H | N |
| 56 | i-Bu | —CH₂CF₃ | Et | H | N |
| 57 | s-Bu | —CH₂CF₃ | Et | H | N |
| 58 | t-Bu | —CH₂CF₃ | Et | H | N |
| 59 | n-Pen | —CH₂CF₃ | Et | H | N |
| 60 | n-Hex | —CH₂CF₃ | Et | H | N |
| 61 | Me | —CH₂CF₃ | n-Pr | H | C |
| 62 | Et | —CH₂CF₃ | n-Pr | H | C |
| 63 | n-Pr | —CH₂CF₃ | n-Pr | H | C |
| 64 | i-Pr | —CH₂CF₃ | n-Pr | H | C |
| 65 | n-Bu | —CH₂CF₃ | n-Pr | H | C |
| 66 | i-Bu | —CH₂CF₃ | n-Pr | H | C |
| 67 | s-Bu | —CH₂CF₃ | n-Pr | H | C |
| 68 | t-Bu | —CH₂CF₃ | n-Pr | H | C |
| 69 | n-Pen | —CH₂CF₃ | n-Pr | H | C |
| 70 | n-Hex | —CH₂CF₃ | n-Pr | H | C |
| 71 | Me | —CH₂CF₃ | n-Pr | H | N |
| 72 | Et | —CH₂CF₃ | n-Pr | H | N |
| 73 | n-Pr | —CH₂CF₃ | n-Pr | H | N |
| 74 | i-Pr | —CH₂CF₃ | n-Pr | H | N |
| 75 | n-Bu | —CH₂CF₃ | n-Pr | H | N |
| 76 | i-Bu | —CH₂CF₃ | n-Pr | H | N |
| 77 | s-Bu | —CH₂CF₃ | n-Pr | H | N |
| 78 | t-Bu | —CH₂CF₃ | n-Pr | H | N |
| 79 | n-Pen | —CH₂CF₃ | n-Pr | H | N |
| 80 | n-Hex | —CH₂CF₃ | n-Pr | H | N |
| 81 | Me | —CH₂CF₃ | n-Bu | H | C |
| 82 | Et | —CH₂CF₃ | n-Bu | H | C |
| 83 | n-Pr | —CH₂CF₃ | n-Bu | H | C |
| 84 | i-Pr | —CH₂CF₃ | n-Bu | H | C |
| 85 | n-Bu | —CH₂CF₃ | n-Bu | H | C |
| 86 | i-Bu | —CH₂CF₃ | n-Bu | H | C |
| 87 | s-Bu | —CH₂CF₃ | n-Bu | H | C |
| 88 | t-Bu | —CH₂CF₃ | n-Bu | H | C |
| 89 | n-Pen | —CH₂CF₃ | n-Bu | H | C |
| 90 | n-Hex | —CH₂CF₃ | n-Bu | H | C |
| 91 | Me | —CH₂CF₃ | n-Bu | H | N |
| 92 | Et | —CH₂CF₃ | n-Bu | H | N |
| 93 | n-Pr | —CH₂CF₃ | n-Bu | H | N |
| 94 | i-Pr | —CH₂CF₃ | n-Bu | H | N |
| 95 | n-Bu | —CH₂CF₃ | n-Bu | H | N |
| 96 | i-Bu | —CH₂CF₃ | n-Bu | H | N |
| 97 | s-Bu | —CH₂CF₃ | n-Bu | H | N |
| 98 | t-Bu | —CH₂CF₃ | n-Bu | H | N |
| 99 | n-Pen | —CH₂CF₃ | n-Bu | H | N |
| 100 | n-Hex | —CH₂CF₃ | n-Bu | H | N |
| 101 | Me | —CH₂CF₃ | —CH₂CF₃ | Me | C |
| 102 | Et | —CH₂CF₃ | —CH₂CF₃ | Me | C |
| 103 | n-Pr | —CH₂CF₃ | —CH₂CF₃ | Me | C |
| 104 | i-Pr | —CH₂CF₃ | —CH₂CF₃ | Me | C |
| 105 | n-Bu | —CH₂CF₃ | —CH₂CF₃ | Me | C |
| 106 | i-Bu | —CH₂CF₃ | —CH₂CF₃ | Me | C |
| 107 | s-Bu | —CH₂CF₃ | —CH₂CF₃ | Me | C |

TABLE 1-continued

| Comp. No. | R¹ | R² | R³ | R⁴ | X |
|---|---|---|---|---|---|
| 108 | t-Bu | —CH₂CF₃ | —CH₂CF₃ | Me | C |
| 109 | n-Pen | —CH₂CF₃ | —CH₂CF₃ | Me | C |
| 110 | n-Hex | —CH₂CF₃ | —CH₂CF₃ | Me | C |
| 111 | Me | —CH₂CF₃ | —CH₂CF₃ | Me | N |
| 112 | Et | —CH₂CF₃ | —CH₂CF₃ | Me | N |
| 113 | n-Pr | —CH₂CF₃ | —CH₂CF₃ | Me | N |
| 114 | i-Pr | —CH₂CF₃ | —CH₂CF₃ | Me | N |
| 115 | n-Bu | —CH₂CF₃ | —CH₂CF₃ | Me | N |
| 116 | i-Bu | —CH₂CF₃ | —CH₂CF₃ | Me | N |
| 117 | s-Bu | —CH₂CF₃ | —CH₂CF₃ | Me | N |
| 118 | t-Bu | —CH₂CF₃ | —CH₂CF₃ | Me | N |
| 119 | n-Pen | —CH₂CF₃ | —CH₂CF₃ | Me | N |
| 120 | n-Hex | —CH₂CF₃ | —CH₂CF₃ | Me | N |
| 121 | Me | Me | —CH₂CF₃ | Me | C |
| 122 | Et | Me | —CH₂CF₃ | Me | C |
| 123 | n-Pr | Me | —CH₂CF₃ | Me | C |
| 124 | i-Pr | Me | —CH₂CF₃ | Me | C |
| 125 | n-Bu | Me | —CH₂CF₃ | Me | C |
| 126 | i-Bu | Me | —CH₂CF₃ | Me | C |
| 127 | s-Bu | Me | —CH₂CF₃ | Me | C |
| 128 | t-Bu | Me | —CH₂CF₃ | Me | C |
| 129 | n-Pen | Me | —CH₂CF₃ | Me | C |
| 130 | n-Hex | Me | —CH₂CF₃ | Me | C |
| 131 | Me | Me | —CH₂CF₃ | Me | N |
| 132 | Et | Me | —CH₂CF₃ | Me | N |
| 133 | n-Pr | Me | —CH₂CF₃ | Me | N |
| 134 | i-Pr | Me | —CH₂CF₃ | Me | N |
| 135 | n-Bu | Me | —CH₂CF₃ | Me | N |
| 136 | i-Bu | Me | —CH₂CF₃ | Me | N |
| 137 | s-Bu | Me | —CH₂CF₃ | Me | N |
| 133 | t-Bu | Me | —CH₂CF₃ | Me | N |
| 139 | n-Pen | Me | —CH₂CF₃ | Me | N |
| 140 | n-Hex | Me | —CH₂CF₃ | Me | N |
| 141 | Me | —CH₂CF₃ | Et | Me | C |
| 142 | Et | —CH₂CF₃ | Et | Me | C |
| 143 | n-Pr | —CH₂CF₃ | Et | Me | C |
| 144 | i-Pr | —CH₂CF₃ | Et | Me | C |
| 145 | n-Bu | —CH₂CF₃ | Et | Me | C |
| 146 | i-Bu | —CH₂CF₃ | Et | Me | C |
| 147 | s-Bu | —CH₂CF₃ | Et | Me | C |
| 148 | t-Bu | —CH₂CF₃ | Et | Me | C |
| 149 | n-Pen | —CH₂CF₃ | Et | Me | C |
| 150 | n-Hex | —CH₂CF₃ | Et | Me | C |
| 151 | Me | —CH₂CF₃ | Et | Me | N |
| 152 | Et | —CH₂CF₃ | Et | Me | N |
| 153 | n-Pr | —CH₂CF₃ | Et | Me | N |
| 154 | i-Pr | —CH₂CF₃ | Et | Me | N |
| 155 | n-Bu | —CH₂CF₃ | Et | Me | N |
| 156 | i-Bu | —CH₂CF₃ | Et | Me | N |
| 157 | s-Bu | —CH₂CF₃ | Et | Me | N |
| 158 | t-Bu | —CH₂CF₃ | Et | Me | N |
| 159 | n-Pen | —CH₂CF₃ | Et | Me | N |
| 160 | n-Hex | —CH₂CF₃ | Et | Me | N |
| 161 | Me | —CH₂CF₃ | n-Pr | Me | C |
| 162 | Et | —CH₂CF₃ | n-Pr | Me | C |
| 163 | n-Pr | —CH₂CF₃ | n-Pr | Me | C |
| 164 | i-Pr | —CH₂CF₃ | n-Pr | Me | C |
| 165 | n-Bu | —CH₂CF₃ | n-Pr | Me | C |
| 166 | i-Bu | —CH₂CF₃ | n-Pr | Me | C |
| 167 | s-Bu | —CH₂CF₃ | n-Pr | Me | C |
| 168 | t-Bu | —CH₂CF₃ | n-Pr | Me | C |
| 169 | n-Pen | —CH₂CF₃ | n-Pr | Me | C |
| 170 | n-Hex | —CH₂CF₃ | n-Pr | Me | C |
| 171 | Me | —CH₂CF₃ | n-Pr | Me | N |
| 172 | Et | —CH₂CF₃ | n-Pr | Me | N |
| 173 | n-Pr | —CH₂CF₃ | n-Pr | Me | N |
| 174 | i-Pr | —CH₂CF₃ | n-Pr | Me | N |
| 175 | n-Bu | —CH₂CF₃ | n-Pr | Me | N |
| 176 | i-Bu | —CH₂CF₃ | n-Pr | Me | N |
| 177 | s-Bu | —CH₂CF₃ | n-Pr | Me | N |
| 178 | t-Bu | —CH₂CF₃ | n-Pr | Me | N |
| 179 | n-Pen | —CH₂CF₃ | n-Pr | Me | N |
| 180 | n-Hex | —CH₂CF₃ | n-Pr | Me | N |
| 181 | Me | —CH₂CF₃ | n-Bu | Me | C |
| 182 | Et | —CH₂CF₃ | n-Bu | Me | C |
| 183 | n-Pr | —CH₂CF₃ | n-Bu | Me | C |
| 184 | i-Pr | —CH₂CF₃ | n-Bu | Me | C |

TABLE 1-continued

| Comp. No. | R¹ | R² | R³ | R⁴ | X |
|---|---|---|---|---|---|
| 185 | n-Bu | —CH₂CF₃ | n-Bu | Me | C |
| 186 | i-Bu | —CH₂CF₃ | n-Bu | Me | C |
| 187 | s-Bu | —CH₂CF₃ | n-Bu | Me | C |
| 188 | t-Bu | —CH₂CF₃ | n-Bu | Me | C |
| 189 | n-Pen | —CH₂CF₃ | n-Bu | Me | C |
| 190 | n-Hex | —CH₂CF₃ | n-Bu | Me | C |
| 191 | Me | —CH₂CF₃ | n-Bu | Me | N |
| 192 | Et | —CH₂CF₃ | n-Bu | Me | N |
| 193 | n-Pr | —CH₂CF₃ | n-Bu | Me | N |
| 194 | i-Pr | —CH₂CF₃ | n-Bu | Me | N |
| 195 | n-Bu | —CH₂CF₃ | n-Bu | Me | N |
| 196 | i-Bu | —CH₂CF₃ | n-Bu | Me | N |
| 197 | s-Bu | —CH₂CF₃ | n-Bu | Me | N |
| 198 | t-Bu | —CH₂CF₃ | n-Bu | Me | N |
| 199 | n-Pen | —CH₂CF₃ | n-Bu | Me | N |
| 200 | n-Hex | —CH₂CF₃ | n-Bu | Me | N |
| 201 | Me | —CH₂CF₃ | —CH₂CF₃ | —CH₂F | C |
| 202 | Et | —CH₂CF₃ | —CH₂CF₃ | —CH₂F | C |
| 203 | n-Pr | —CH₂CF₃ | —CH₂CF₃ | —CH₂F | C |
| 204 | i-Pr | —CH₂CF₃ | —CH₂CF₃ | —CH₂F | C |
| 205 | n-Bu | —CH₂CF₃ | —CH₂CF₃ | —CH₂F | C |
| 206 | i-Bu | —CH₂CF₃ | —CH₂CF₃ | —CH₂F | C |
| 207 | s-Bu | —CH₂CF₃ | —CH₂CF₃ | —CH₂F | C |
| 208 | t-Bu | —CH₂CF₃ | —CH₂CF₃ | —CH₂F | C |
| 209 | n-Pen | —CH₂CF₃ | —CH₂CF₃ | —CH₂F | C |
| 210 | n-Hex | —CH₂CF₃ | —CH₂CF₃ | —CH₂F | C |
| 211 | Me | —CH₂CF₃ | —CH₂CF₃ | —CH₂F | N |
| 212 | Et | —CH₂CF₃ | —CH₂CF₃ | —CH₂F | N |
| 213 | n-Pr | —CH₂CF₃ | —CH₂CF₃ | —CH₂F | N |
| 214 | i-Pr | —CH₂CF₃ | —CH₂CF₃ | —CH₂F | N |
| 215 | n-Bu | —CH₂CF₃ | —CH₂CF₃ | —CH₂F | N |
| 216 | i-Bu | —CH₂CF₃ | —CH₂CF₃ | —CH₂F | N |
| 217 | s-Bu | —CH₂CF₃ | —CH₂CF₃ | —CH₂F | N |
| 218 | t-Bu | —CH₂CF₃ | —CH₂CF₃ | —CH₂F | N |
| 219 | n-Pen | —CH₂CF₃ | —CH₂CF₃ | —CH₂F | N |
| 220 | n-Hex | —CH₂CF₃ | —CH₂CF₃ | —CH₂F | N |
| 221 | Me | Me | —CH₂CF₃ | —CH₂F | C |
| 222 | Et | Me | —CH₂CF₃ | —CH₂F | C |
| 223 | n-Pr | Me | —CH₂CF₃ | —CH₂F | C |
| 224 | i-Pr | Me | —CH₂CF₃ | —CH₂F | C |
| 225 | n-Bu | Me | —CH₂CF₃ | —CH₂F | C |
| 226 | i-Bu | Me | —CH₂CF₃ | —CH₂F | C |
| 227 | s-Bu | Me | —CH₂CF₃ | —CH₂F | C |
| 228 | t-Bu | Me | —CH₂CF₃ | —CH₂F | C |
| 229 | n-Pen | Me | —CH₂CF₃ | —CH₂F | C |
| 230 | n-Hex | Me | —CH₂CF₃ | —CH₂F | C |
| 231 | Me | Me | —CH₂CF₃ | —CH₂F | N |
| 232 | Et | Me | —CH₂CF₃ | —CH₂F | N |
| 233 | n-Pr | Me | —CH₂CF₃ | —CH₂F | N |
| 234 | i-Pr | Me | —CH₂CF₃ | —CH₂F | N |
| 235 | n-Bu | Me | —CH₂CF₃ | —CH₂F | N |
| 236 | i-Bu | Me | —CH₂CF₃ | —CH₂F | N |
| 237 | s-Bu | Me | —CH₂CF₃ | —CH₂F | N |
| 238 | t-Bu | Me | —CH₂CF₃ | —CH₂F | N |
| 239 | n-Pen | Me | —CH₂CF₃ | —CH₂F | N |
| 240 | n-Hex | Me | —CH₂CF₃ | —CH₂F | N |
| 241 | Me | —CH₂CF₃ | Et | —CH₂F | C |
| 242 | Et | —CH₂CF₃ | Et | —CH₂F | C |
| 243 | n-Pr | —CH₂CF₃ | Et | —CH₂F | C |
| 244 | i-Pr | —CH₂CF₃ | Et | —CH₂F | C |
| 245 | n-Bu | —CH₂CF₃ | Et | —CH₂F | C |
| 246 | i-Bu | —CH₂CF₃ | Et | —CH₂F | C |
| 247 | s-Bu | —CH₂CF₃ | Et | —CH₂F | C |
| 248 | t-Bu | —CH₂CF₃ | Et | —CH₂F | C |
| 249 | n-Pen | —CH₂CF₃ | Et | —CH₂F | C |
| 250 | n-Hex | —CH₂CF₃ | Et | —CH₂F | C |
| 251 | Me | —CH₂CF₃ | Et | —CH₂F | N |
| 252 | Et | —CH₂CF₃ | Et | —CH₂F | N |
| 253 | n-Pr | —CH₂CF₃ | Et | —CH₂F | N |
| 254 | i-Pr | —CH₂CF₃ | Et | —CH₂F | N |
| 255 | n-Bu | —CH₂CF₃ | Et | —CH₂F | N |
| 256 | i-Bu | —CH₂CF₃ | Et | —CH₂F | N |
| 257 | s-Bu | —CH₂CF₃ | Et | —CH₂F | N |
| 258 | t-Bu | —CH₂CF₃ | Et | —CH₂F | N |
| 259 | n-Pen | —CH₂CF₃ | Et | —CH₂F | N |
| 260 | n-Hex | —CH₂CF₃ | Et | —CH₂F | N |
| 261 | Me | —CH₂CF₃ | n-Pr | —CH₂F | C |

TABLE 1-continued

| Comp. No. | R¹ | R² | R³ | R⁴ | X |
|---|---|---|---|---|---|
| 262 | Et | —CH$_2$CF$_3$ | n-Pr | —CH$_2$F | C |
| 263 | n-Pr | —CH$_2$CF$_3$ | n-Pr | —CH$_2$F | C |
| 264 | i-Pr | —CH$_2$CF$_3$ | n-Pr | —CH$_2$F | C |
| 265 | n-Bu | —CH$_2$CF$_3$ | n-Pr | —CH$_2$F | C |
| 266 | i-Bu | —CH$_2$CF$_3$ | n-Pr | —CH$_2$F | C |
| 267 | s-Bu | —CH$_2$CF$_3$ | n-Pr | —CH$_2$F | C |
| 268 | t-Bu | —CH$_2$CF$_3$ | n-Pr | —CH$_2$F | C |
| 269 | n-Pen | —CH$_2$CF$_3$ | n-Pr | —CH$_2$F | C |
| 270 | n-Hex | —CH$_2$CF$_3$ | n-Pr | —CH$_2$F | C |
| 271 | Me | —CH$_2$CF$_3$ | n-Pr | —CH$_2$F | N |
| 272 | Et | —CH$_2$CF$_3$ | n-Pr | —CH$_2$F | N |
| 273 | n-Pr | —CH$_2$CF$_3$ | n-Pr | —CH$_2$F | N |
| 274 | i-Pr | —CH$_2$CF$_3$ | n-Pr | —CH$_2$F | N |
| 275 | n-Bu | —CH$_2$CF$_3$ | n-Pr | —CH$_2$F | N |
| 276 | i-Bu | —CH$_2$CF$_3$ | n-Pr | —CH$_2$F | N |
| 277 | s-Bu | —CH$_2$CF$_3$ | n-Pr | —CH$_2$F | N |
| 278 | t-Bu | —CH$_2$CF$_3$ | n-Pr | —CH$_2$F | N |
| 279 | n-Pen | —CH$_2$CF$_3$ | n-Pr | —CH$_2$F | N |
| 280 | n-Hex | —CH$_2$CF$_3$ | n-Pr | —CH$_2$F | N |
| 281 | Me | —CH$_2$CF$_3$ | n-Bu | —CH$_2$F | C |
| 282 | Et | —CH$_2$CF$_3$ | n-Bu | —CH$_2$F | C |
| 283 | n-Pr | —CH$_2$CF$_3$ | n-Bu | —CH$_2$F | C |
| 284 | i-Pr | —CH$_2$CF$_3$ | n-Bu | —CH$_2$F | C |
| 285 | n-Bu | —CH$_2$CF$_3$ | n-Bu | —CH$_2$F | C |
| 286 | i-Bu | —CH$_2$CF$_3$ | n-Bu | —CH$_2$F | C |
| 287 | s-Bu | —CH$_2$CF$_3$ | n-Bu | —CH$_2$F | C |
| 288 | t-Bu | —CH$_2$CF$_3$ | n-Bu | —CH$_2$F | C |
| 289 | n-Pen | —CH$_2$CF$_3$ | n-Bu | —CH$_2$F | C |
| 290 | n-Hex | —CH$_2$CF$_3$ | n-Bu | —CH$_2$F | C |
| 291 | Me | —CH$_2$CF$_3$ | n-Bu | —CH$_2$F | N |
| 292 | Et | —CH$_2$CF$_3$ | n-Bu | —CH$_2$F | N |
| 293 | n-Pr | —CH$_2$CF$_3$ | n-Bu | —CH$_2$F | N |
| 294 | i-Pr | —CH$_2$CF$_3$ | n-Bu | —CH$_2$F | N |
| 295 | n-Bu | —CH$_2$CF$_3$ | n-Bu | —CH$_2$F | N |
| 296 | i-Bu | —CH$_2$CF$_3$ | n-Bu | —CH$_2$F | N |
| 297 | s-Bu | —CH$_2$CF$_3$ | n-Bu | —CH$_2$F | N |
| 298 | t-Bu | —CH$_2$CF$_3$ | n-Bu | —CH$_2$F | N |
| 299 | n-Pen | —CH$_2$CF$_3$ | n-Bu | —CH$_2$F | N |
| 300 | n-Hex | —CH$_2$CF$_3$ | n-Bu | —CH$_2$F | N |
| 301 | Me | —CH$_2$CF$_3$ | —CH$_2$CF$_3$ | —CH$_2$OH | C |
| 302 | Et | —CH$_2$CF$_3$ | —CH$_2$CF$_3$ | —CH$_2$OH | C |
| 303 | n-Pr | —CH$_2$CF$_3$ | —CH$_2$CF$_3$ | —CH$_2$OH | C |
| 304 | i-Pr | —CH$_2$CF$_3$ | —CH$_2$CF$_3$ | —CH$_2$OH | C |
| 305 | n-Bu | —CH$_2$CF$_3$ | —CH$_2$CF$_3$ | —CH$_2$OH | C |
| 306 | i-Bu | —CH$_2$CF$_3$ | —CH$_2$CF$_3$ | —CH$_2$OH | C |
| 307 | s-Bu | —CH$_2$CF$_3$ | —CH$_2$CF$_3$ | —CH$_2$OH | C |
| 308 | t-Bu | —CH$_2$CF$_3$ | —CH$_2$CF$_3$ | —CH$_2$OH | C |
| 309 | n-Pen | —CH$_2$CF$_3$ | —CH$_2$CF$_3$ | —CH$_2$OH | C |
| 310 | n-Hex | —CH$_2$CF$_3$ | —CH$_2$CF$_3$ | —CH$_2$OH | C |
| 311 | Me | —CH$_2$CF$_3$ | —CH$_2$CF$_3$ | —CH$_2$OH | N |
| 312 | Et | —CH$_2$CF$_3$ | —CH$_2$CF$_3$ | —CH$_2$OH | N |
| 313 | n-Pr | —CH$_2$CF$_3$ | —CH$_2$CF$_3$ | —CH$_2$OH | N |
| 314 | i-Pr | —CH$_2$CF$_3$ | —CH$_2$CF$_3$ | —CH$_2$OH | N |
| 315 | n-Bu | —CH$_2$CF$_3$ | —CH$_2$CF$_3$ | —CH$_2$OH | N |
| 316 | i-Bu | —CH$_2$CF$_3$ | —CH$_2$CF$_3$ | —CH$_2$OH | N |
| 317 | s-Bu | —CH$_2$CF$_3$ | —CH$_2$CF$_3$ | —CH$_2$OH | N |
| 318 | t-Bu | —CH$_2$CF$_3$ | —CH$_2$CF$_3$ | —CH$_2$OH | N |
| 319 | n-Pen | —CH$_2$CF$_3$ | —CH$_2$CF$_3$ | —CH$_2$OH | N |
| 320 | n-Hex | —CH$_2$CF$_3$ | —CH$_2$CF$_3$ | —CH$_2$OH | N |
| 321 | Me | Me | —CH$_2$CF$_3$ | —CH$_2$OH | C |
| 322 | Et | Me | —CH$_2$CF$_3$ | —CH$_2$OH | C |
| 323 | n-Pr | Me | —CH$_2$CF$_3$ | —CH$_2$OH | C |
| 324 | i-Pr | Me | —CH$_2$CF$_3$ | —CH$_2$OH | C |
| 325 | n-Bu | Me | —CH$_2$CF$_3$ | —CH$_2$OH | C |
| 326 | i-Bu | Me | —CH$_2$CF$_3$ | —CH$_2$OH | C |
| 327 | s-Bu | Me | —CH$_2$CF$_3$ | —CH$_2$OH | C |
| 328 | t-Bu | Me | —CH$_2$CF$_3$ | —CH$_2$OH | C |
| 329 | n-Pen | Me | —CH$_2$CF$_3$ | —CH$_2$OH | C |
| 330 | n-Hex | Me | —CH$_2$CF$_3$ | —CH$_2$OH | C |
| 331 | Me | Me | —CH$_2$CF$_3$ | —CH$_2$OH | N |
| 332 | Et | Me | —CH$_2$CF$_3$ | —CH$_2$OH | N |
| 333 | n-Pr | Me | —CH$_2$CF$_3$ | —CH$_2$OH | N |
| 334 | i-Pr | Me | —CH$_2$CF$_3$ | —CH$_2$OH | N |
| 335 | n-Bu | Me | —CH$_2$CF$_3$ | —CH$_2$OH | N |
| 336 | i-Bu | Me | —CH$_2$CF$_3$ | —CH$_2$OH | N |
| 337 | s-Bu | Me | —CH$_2$CF$_3$ | —CH$_2$OH | N |
| 338 | t-Bu | Me | —CH$_2$CF$_3$ | —CH$_2$OH | N |

TABLE 1-continued

| Comp. No. | R¹ | R² | R³ | R⁴ | X |
|---|---|---|---|---|---|
| 339 | n-Pen | Me | —CH$_2$CF$_3$ | —CH$_2$OH | N |
| 340 | n-Hex | Me | —CH$_2$CF$_3$ | —CH$_2$OH | N |
| 341 | Me | —CH$_2$CF$_3$ | Et | —CH$_2$OH | C |
| 342 | Et | —CH$_2$CF$_3$ | Et | —CH$_2$OH | C |
| 343 | n-Pr | —CH$_2$CF$_3$ | Et | —CH$_2$OH | C |
| 344 | i-Pr | —CH$_2$CF$_3$ | Et | —CH$_2$OH | C |
| 345 | n-Bu | —CH$_2$CF$_3$ | Et | —CH$_2$OH | C |
| 346 | i-Bu | —CH$_2$CF$_3$ | Et | —CH$_2$OH | C |
| 347 | s-Bu | —CH$_2$CF$_3$ | Et | —CH$_2$OH | C |
| 348 | t-Bu | —CH$_2$CF$_3$ | Et | —CH$_2$OH | C |
| 349 | n-Pen | —CH$_2$CF$_3$ | Et | —CH$_2$OH | C |
| 350 | n-Hex | —CH$_2$CF$_3$ | Et | —CH$_2$OH | C |
| 351 | Me | —CH$_2$CF$_3$ | Et | —CH$_2$OH | N |
| 352 | Et | —CH$_2$CF$_3$ | Et | —CH$_2$OH | N |
| 353 | n-Pr | —CH$_2$CF$_3$ | Et | —CH$_2$OH | N |
| 354 | i-Pr | —CH$_2$CF$_3$ | Et | —CH$_2$OH | N |
| 355 | n-Bu | —CH$_2$CF$_3$ | Et | —CH$_2$OH | N |
| 356 | i-Bu | —CH$_2$CF$_3$ | Et | —CH$_2$OH | N |
| 357 | s-Bu | —CH$_2$CF$_3$ | Et | —CH$_2$OH | N |
| 358 | t-Bu | —CH$_2$CF$_3$ | Et | —CH$_2$OH | N |
| 359 | n-Pen | —CH$_2$CF$_3$ | Et | —CH$_2$OH | N |
| 360 | n-Hex | —CH$_2$CF$_3$ | Et | —CH$_2$OH | N |
| 361 | Me | —CH$_2$CF$_3$ | n-Pr | —CH$_2$OH | C |
| 362 | Et | —CH$_2$CF$_3$ | n-Pr | —CH$_2$OH | C |
| 363 | n-Pr | —CH$_2$CF$_3$ | n-Pr | —CH$_2$OH | C |
| 364 | i-Pr | —CH$_2$CF$_3$ | n-Pr | —CH$_2$OH | C |
| 365 | n-Bu | —CH$_2$CF$_3$ | n-Pr | —CH$_2$OH | C |
| 366 | i-Bu | —CH$_2$CF$_3$ | n-Pr | —CH$_2$OH | C |
| 367 | s-Bu | —CH$_2$CF$_3$ | n-Pr | —CH$_2$OH | C |
| 368 | t-Bu | —CH$_2$CF$_3$ | n-Pr | —CH$_2$OH | C |
| 369 | n-Pen | —CH$_2$CF$_3$ | n-Pr | —CH$_2$OH | C |
| 370 | n-Hex | —CH$_2$CF$_3$ | n-Pr | —CH$_2$OH | C |
| 371 | Me | —CH$_2$CF$_3$ | n-Pr | —CH$_2$OH | N |
| 372 | Et | —CH$_2$CF$_3$ | n-Pr | —CH$_2$OH | N |
| 373 | n-Pr | —CH$_2$CF$_3$ | n-Pr | —CH$_2$OH | N |
| 374 | i-Pr | —CH$_2$CF$_3$ | n-Pr | —CH$_2$OH | N |
| 375 | n-Bu | —CH$_2$CF$_3$ | n-Pr | —CH$_2$OH | N |
| 376 | i-Bu | —CH$_2$CF$_3$ | n-Pr | —CH$_2$OH | N |
| 377 | s-Bu | —CH$_2$CF$_3$ | n-Pr | —CH$_2$OH | N |
| 378 | t-Bu | —CH$_2$CF$_3$ | n-Pr | —CH$_2$OH | N |
| 379 | n-Pen | —CH$_2$CF$_3$ | n-Pr | —CH$_2$OH | N |
| 380 | n-Hex | —CH$_2$CF$_3$ | n-Pr | —CH$_2$OH | N |
| 381 | Me | —CH$_2$CF$_3$ | n-Bu | —CH$_2$OH | C |
| 382 | Et | —CH$_2$CF$_3$ | n-Bu | —CH$_2$OH | C |
| 383 | n-Pr | —CH$_2$CF$_3$ | n-Bu | —CH$_2$OH | C |
| 384 | i-Pr | —CH$_2$CF$_3$ | n-Bu | —CH$_2$OH | C |
| 385 | n-Bu | —CH$_2$CF$_3$ | n-Bu | —CH$_2$OH | C |
| 386 | i-Bu | —CH$_2$CF$_3$ | n-Bu | —CH$_2$OH | C |
| 387 | s-Bu | —CH$_2$CF$_3$ | n-Bu | —CH$_2$OH | C |
| 388 | t-Bu | —CH$_2$CF$_3$ | n-Bu | —CH$_2$OH | C |
| 389 | n-Pen | —CH$_2$CF$_3$ | n-Bu | —CH$_2$OH | C |
| 390 | n-Hex | —CH$_2$CF$_3$ | n-Bu | —CH$_2$OH | C |
| 391 | Me | —CH$_2$CF$_3$ | n-Bu | —CH$_2$OH | N |
| 392 | Et | —CH$_2$CF$_3$ | n-Bu | —CH$_2$OH | N |
| 393 | n-Pr | —CH$_2$CF$_3$ | n-Bu | —CH$_2$OH | N |
| 394 | i-Pr | —CH$_2$CF$_3$ | n-Bu | —CH$_2$OH | N |
| 395 | n-Bu | —CH$_2$CF$_3$ | n-Bu | —CH$_2$OH | N |
| 396 | i-Bu | —CH$_2$CF$_3$ | n-Bu | —CH$_2$OH | N |
| 397 | s-Bu | —CH$_2$CF$_3$ | n-Bu | —CH$_2$OH | N |
| 398 | t-Bu | —CH$_2$CF$_3$ | n-Bu | —CH$_2$OH | N |
| 399 | n-Pen | —CH$_2$CF$_3$ | n-Bu | —CH$_2$OH | N |
| 400 | n-Hex | —CH$_2$CF$_3$ | n-Bu | —CH$_2$OH | N |
| 401 | Me | —CH$_2$OC(=O)C(CH$_3$)$_3$ | —CH$_2$OC(=O)C(CH$_3$)$_3$ | H | C |
| 402 | Et | —CH$_2$OC(=O)C(CH$_3$)$_3$ | —CH$_2$OC(=O)C(CH$_3$)$_3$ | H | C |

TABLE 1-continued

| Comp. No. | R¹ | R² | R³ | R⁴ | X |
|---|---|---|---|---|---|
| 403 | n-Pr | —CH₂OC(=O)C(CH₃)₃ | —CH₂OC(=O)C(CH₃)₃ | H | C |
| 404 | i-Pr | —CH₂OC(=O)C(CH₃)₃ | —CH₂OC(=O)C(CH₃)₃ | H | C |
| 405 | n-Bu | —CH₂OC(=O)C(CH₃)₃ | —CH₂OC(=O)C(CH₃)₃ | H | C |
| 406 | i-Bu | —CH₂OC(=O)C(CH₃)₃ | —CH₂OC(=O)C(CH₃)₃ | H | C |
| 407 | s-Bu | —CH₂OC(=O)C(CH₃)₃ | —CH₂OC(=O)C(CH₃)₃ | H | C |
| 408 | t-Bu | —CH₂OC(=O)C(CH₃)₃ | —CH₂OC(=O)C(CH₃)₃ | H | C |
| 409 | n-Pen | —CH₂OC(=O)C(CH₃)₃ | —CH₂OC(=O)C(CH₃)₃ | H | C |
| 410 | n-Hex | —CH₂OC(=O)C(CH₃)₃ | —CH₂OC(=O)C(CH₃)₃ | H | C |
| 411 | Me | —CH₂OC(=O)C(CH₃)₃ | —CH₂OC(=O)C(CH₃)₃ | Me | C |
| 412 | Et | —CH₂OC(=O)C(CH₃)₃ | —CH₂OC(=O)C(CH₃)₃ | Me | C |
| 413 | n-Pr | —CH₂OC(=O)C(CH₃)₃ | —CH₂OC(=O)C(CH₃)₃ | Me | C |
| 414 | i-Pr | —CH₂OC(=O)C(CH₃)₃ | —CH₂OC(=O)C(CH₃)₃ | Me | C |

TABLE 1-continued

| Comp. No. | R¹ | R² | R³ | R⁴ | X |
|---|---|---|---|---|---|
| 415 | n-Bu | —CH₂OC(O)C(CH₃)₃ | —CH₂OC(O)C(CH₃)₃ | Me | C |
| 416 | i-Bu | —CH₂OC(O)C(CH₃)₃ | —CH₂OC(O)C(CH₃)₃ | Me | C |
| 417 | s-Bu | —CH₂OC(O)C(CH₃)₃ | —CH₂OC(O)C(CH₃)₃ | Me | C |
| 418 | t-Bu | —CH₂OC(O)C(CH₃)₃ | —CH₂OC(O)C(CH₃)₃ | Me | C |
| 419 | n-Pen | —CH₂OC(O)C(CH₃)₃ | —CH₂OC(O)C(CH₃)₃ | Me | C |
| 420 | n-Hex | —CH₂OC(O)C(CH₃)₃ | —CH₂OC(O)C(CH₃)₃ | Me | C |
| 421 | Me | —CH₂OC(O)C(CH₃)₃ | —CH₂OC(O)C(CH₃)₃ | —CH₂F | C |
| 422 | Et | —CH₂OC(O)C(CH₃)₃ | —CH₂OC(O)C(CH₃)₃ | —CH₂F | C |
| 423 | n-Pr | —CH₂OC(O)C(CH₃)₃ | —CH₂OC(O)C(CH₃)₃ | —CH₂F | C |
| 424 | i-Pr | —CH₂OC(O)C(CH₃)₃ | —CH₂OC(O)C(CH₃)₃ | —CH₂F | C |
| 425 | n-Bu | —CH₂OC(O)C(CH₃)₃ | —CH₂OC(O)C(CH₃)₃ | —CH₂F | C |
| 426 | i-Bu | —CH₂OC(O)C(CH₃)₃ | —CH₂OC(O)C(CH₃)₃ | —CH₂F | C |

TABLE 1-continued

| Comp. No. | R¹ | R² | R³ | R⁴ | X |
|---|---|---|---|---|---|
| 427 | s-Bu | —CH₂OC(O)C(CH₃)₃ | —CH₂OC(O)C(CH₃)₃ | —CH₂F | C |
| 428 | t-Bu | —CH₂OC(O)C(CH₃)₃ | —CH₂OC(O)C(CH₃)₃ | —CH₂F | C |
| 429 | n-Pen | —CH₂OC(O)C(CH₃)₃ | —CH₂OC(O)C(CH₃)₃ | —CH₂F | C |
| 430 | n-Hex | —CH₂OC(O)C(CH₃)₃ | —CH₂OC(O)C(CH₃)₃ | —CH₂F | C |
| 431 | Me | —CH₂OC(O)C(CH₃)₃ | —CH₂OC(O)C(CH₃)₃ | —CH₂OH | C |
| 432 | Et | —CH₂OC(O)C(CH₃)₃ | —CH₂OC(O)C(CH₃)₃ | —CH₂OH | C |
| 433 | n-Pr | —CH₂OC(O)C(CH₃)₃ | —CH₂OC(O)C(CH₃)₃ | —CH₂OH | C |
| 434 | i-Pr | —CH₂OC(O)C(CH₃)₃ | —CH₂OC(O)C(CH₃)₃ | —CH₂OH | C |
| 435 | n-Bu | —CH₂OC(O)C(CH₃)₃ | —CH₂OC(O)C(CH₃)₃ | —CH₂OH | C |
| 436 | i-Bu | —CH₂OC(O)C(CH₃)₃ | —CH₂OC(O)C(CH₃)₃ | —CH₂OH | C |
| 437 | s-Bu | —CH₂OC(O)C(CH₃)₃ | —CH₂OC(O)C(CH₃)₃ | —CH₂OH | C |
| 438 | t-Bu | —CH₂OC(O)C(CH₃)₃ | —CH₂OC(O)C(CH₃)₃ | —CH₂OH | C |

TABLE 1-continued

| Comp. No. | R¹ | R² | R³ | R⁴ | X |
|---|---|---|---|---|---|
| 439 | n-Pen | —CH₂OC(O)C(CH₃)₃ | —CH₂OC(O)C(CH₃)₃ | —CH₂OH | C |
| 440 | n-Hex | —CH₂OC(O)C(CH₃)₃ | —CH₂OC(O)C(CH₃)₃ | —CH₂OH | C |
| 441 | Me | —CH₂CH₂SC(O)CH(CH₃)₂ | —CH₂CH₂SC(O)CH(CH₃)₂ | H | C |
| 442 | Et | —CH₂CH₂SC(O)CH(CH₃)₂ | —CH₂CH₂SC(O)CH(CH₃)₂ | H | C |
| 443 | n-Pr | —CH₂CH₂SC(O)CH(CH₃)₂ | —CH₂CH₂SC(O)CH(CH₃)₂ | H | C |
| 444 | i-Pr | —CH₂CH₂SC(O)CH(CH₃)₂ | —CH₂CH₂SC(O)CH(CH₃)₂ | H | C |
| 445 | n-Bu | —CH₂CH₂SC(O)CH(CH₃)₂ | —CH₂CH₂SC(O)CH(CH₃)₂ | H | C |
| 446 | i-Bu | —CH₂CH₂SC(O)CH(CH₃)₂ | —CH₂CH₂SC(O)CH(CH₃)₂ | H | C |
| 447 | s-Bu | —CH₂CH₂SC(O)CH(CH₃)₂ | —CH₂CH₂SC(O)CH(CH₃)₂ | H | C |
| 448 | t-Bu | —CH₂CH₂SC(O)CH(CH₃)₂ | —CH₂CH₂SC(O)CH(CH₃)₂ | H | C |
| 449 | n-Pen | —CH₂CH₂SC(O)CH(CH₃)₂ | —CH₂CH₂SC(O)CH(CH₃)₂ | H | C |
| 450 | n-Hex | —CH₂CH₂SC(O)CH(CH₃)₂ | —CH₂CH₂SC(O)CH(CH₃)₂ | H | C |
| 451 | Me | —CH₂CH₂SC(O)CH(CH₃)₂ | —CH₂CH₂SC(O)CH(CH₃)₂ | Me | C |

TABLE 1-continued

| Comp. No. | R¹ | R² | R³ | R⁴ | X |
|---|---|---|---|---|---|
| 452 | Et | —CH₂CH₂SC(=O)CH(CH₃)₂ | —CH₂CH₂SC(=O)CH(CH₃)₂ | Me | C |
| 453 | n-Pr | —CH₂CH₂SC(=O)CH(CH₃)₂ | —CH₂CH₂SC(=O)CH(CH₃)₂ | Me | C |
| 454 | i-Pr | —CH₂CH₂SC(=O)CH(CH₃)₂ | —CH₂CH₂SC(=O)CH(CH₃)₂ | Me | C |
| 455 | n-Bu | —CH₂CH₂SC(=O)CH(CH₃)₂ | —CH₂CH₂SC(=O)CH(CH₃)₂ | Me | C |
| 456 | i-Bu | —CH₂CH₂SC(=O)CH(CH₃)₂ | —CH₂CH₂SC(=O)CH(CH₃)₂ | Me | C |
| 457 | s-Bu | —CH₂CH₂SC(=O)CH(CH₃)₂ | —CH₂CH₂SC(=O)CH(CH₃)₂ | Me | C |
| 458 | t-Bu | —CH₂CH₂SC(=O)CH(CH₃)₂ | —CH₂CH₂SC(=O)CH(CH₃)₂ | Me | C |
| 459 | n-Pen | —CH₂CH₂SC(=O)CH(CH₃)₂ | —CH₂CH₂SC(=O)CH(CH₃)₂ | Me | C |
| 460 | n-Hex | —CH₂CH₂SC(=O)CH(CH₃)₂ | —CH₂CH₂SC(=O)CH(CH₃)₂ | Me | C |
| 461 | Me | —CH₂CH₂SC(=O)CH(CH₃)₂ | —CH₂CH₂SC(=O)CH(CH₃)₂ | —CH₂F | C |
| 462 | Et | —CH₂CH₂SC(=O)CH(CH₃)₂ | —CH₂CH₂SC(=O)CH(CH₃)₂ | —CH₂F | C |
| 463 | n-Pr | —CH₂CH₂SC(=O)CH(CH₃)₂ | —CH₂CH₂SC(=O)CH(CH₃)₂ | —CH₂F | C |
| 464 | i-Pr | —CH₂CH₂SC(=O)CH(CH₃)₂ | —CH₂CH₂SC(=O)CH(CH₃)₂ | —CH₂F | C |

TABLE 1-continued
| Comp. No. | R¹ | R² | R³ | R⁴ | X |
|---|---|---|---|---|---|
| 465 | n-Bu | 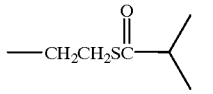 | 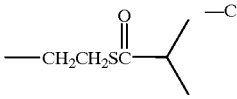 | —CH₂F | C |
| 466 | i-Bu | 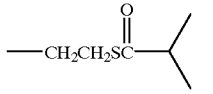 |  | —CH₂F | C |
| 467 | s-Bu | 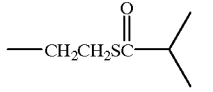 |  | —CH₂F | C |
| 468 | t-Bu | 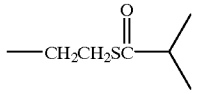 | 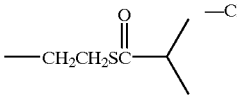 | —CH₂F | C |
| 469 | n-Pen | 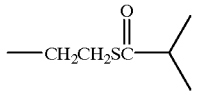 | 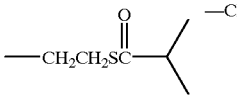 | —CH₂F | C |
| 470 | n-Hex | 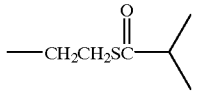 | 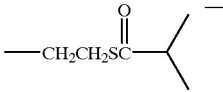 | —CH₂F | C |
| 471 | Me | 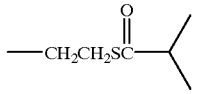 | 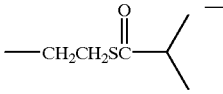 | —CH₂OH | C |
| 472 | Et | 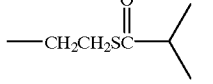 | 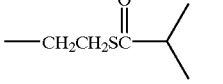 | —CH₂OH | C |
| 473 | n-Pr | 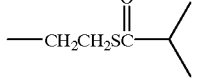 | 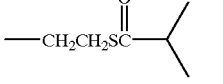 | —CH₂OH | C |
| 474 | i-Pr | 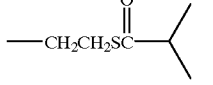 | 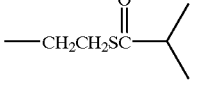 | —CH₂OH | C |
| 475 | n-Bu | 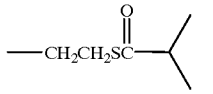 | 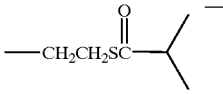 | —CH₂OH | C |
| 476 | i-Bu | 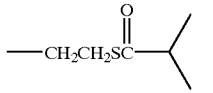 | 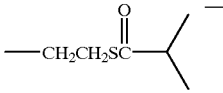 | —CH₂OH | C |
| 477 | s-Bu | 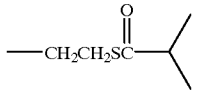 | 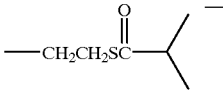 | —CH₂OH | C |

TABLE 1-continued
| Comp. No. | R¹ | R² | R³ | R⁴ | X |
|---|---|---|---|---|---|
| 478 | t-Bu | 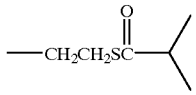 | 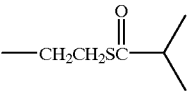 | —CH₂OH | C |
| 479 | n-Pen | 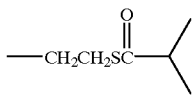 | 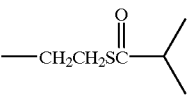 | —CH₂OH | C |
| 480 | n-Hex | 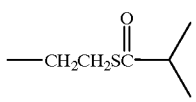 |  | —CH₂OH | C |
| 481 | 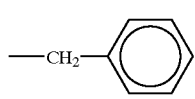 | —CH₂CF₃ | —CH₂CF₃ | H | C |
| 482 | 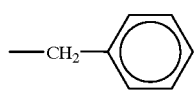 | —CH₂CF₃ | —CH₂CF₃ | H | N |
| 483 | 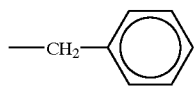 | —CH₂CF₃ | Me | H | C |
| 484 | 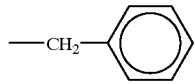 | —CH₂CF₃ | Me | H | N |
| 485 | 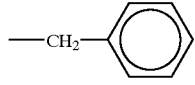 | —CH₂CF₃ | Et | H | C |
| 486 | 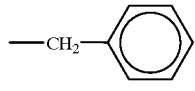 | —CH₂CF₃ | Et | H | N |
| 487 | 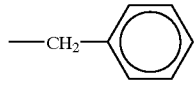 | —CH₂CF₃ | n-Pr | H | C |
| 488 | 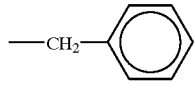 | —CH₂CF₃ | n-Pr | H | N |
| 489 | 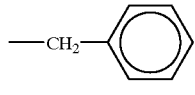 | —CH₂CF₃ | n-Bu | H | C |
| 490 | 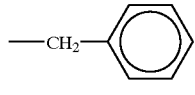 | —CH₂CF₃ | n-Bu | H | N |

TABLE 1-continued
| Comp. No. | R¹ | R² | R³ | R⁴ | X |
|---|---|---|---|---|---|
| 491 | 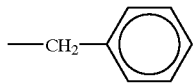 | —CH$_2$CF$_3$ | —CH$_2$CF$_3$ | Me | C |
| 492 | 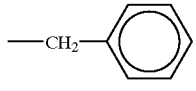 | —CH$_2$CF$_3$ | —CH$_2$CF$_3$ | Me | N |
| 493 | 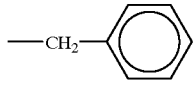 | —CH$_2$CF$_3$ | Me | Me | C |
| 494 | 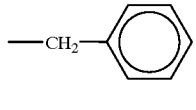 | —CH$_2$CF$_3$ | Me | Me | N |
| 495 | 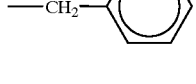 | —CH$_2$CF$_3$ | Et | Me | C |
| 496 | 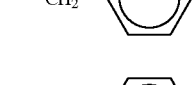 | —CH$_2$CF$_3$ | Et | Me | N |
| 497 |  | —CH$_2$CF$_3$ | n-Pr | Me | C |
| 498 | 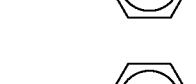 | —CH$_2$CF$_3$ | n-Pr | Me | N |
| 499 | 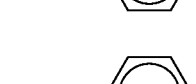 | —CH$_2$CF$_3$ | n-Bu | Me | C |
| 500 | 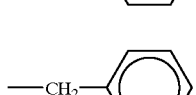 | —CH$_2$CF$_3$ | n-Bu | Me | N |
| 501 | 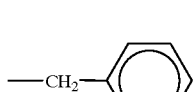 | —CH$_2$CF$_3$ | —CH$_2$CF$_3$ | —CH$_2$F | C |
| 502 | 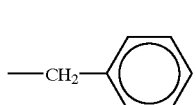 | —CH$_2$CF$_3$ | —CH$_2$CF$_3$ | —CH$_2$F | N |
| 503 | 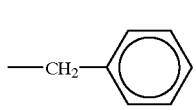 | —CH$_2$CF$_3$ | Me | —CH$_2$F | C |
| 504 |  | —CH$_2$CF$_3$ | Me | —CH$_2$F | N |

TABLE 1-continued

| Comp. No. | R¹ | R² | R³ | R⁴ | X |
|---|---|---|---|---|---|
| 505 | —CH₂—C₆H₅ | —CH₂CF₃ | Et | —CH₂F | C |
| 506 | —CH₂—C₆H₅ | —CH₂CF₃ | Et | —CH₂F | N |
| 507 | —CH₂—C₆H₅ | —CH₂CF₃ | n-Pr | —CH₂F | C |
| 508 | —CH₂—C₆H₅ | —CH₂CF₃ | n-Pr | —CH₂F | N |
| 509 | —CH₂—C₆H₅ | —CH₂CF₃ | n-Bu | —CH₂F | C |
| 510 | —CH₂—C₆H₅ | —CH₂CF₃ | n-Bu | —CH₂F | N |
| 511 | —CH₂—C₆H₅ | —CH₂CF₃ | —CH₂CF₃ | —CH₂OH | C |
| 512 | —CH₂—C₆H₅ | —CH₂CF₃ | —CH₂CF₃ | —CH₂OH | N |
| 513 | —CH₂—C₆H₅ | —CH₂CF₃ | Me | —CH₂OH | C |
| 514 | —CH₂—C₆H₅ | —CH₂CF₃ | Me | —CH₂OH | N |
| 515 | —CH₂—C₆H₅ | —CH₂CF₃ | Et | —CH₂OH | C |
| 516 | —CH₂—C₆H₅ | —CH₂CF₃ | Et | —CH₂OH | N |
| 517 | —CH₂—C₆H₅ | —CH₂CF₃ | n-Pr | —CH₂OH | C |

TABLE 1-continued

| Comp. No. | R¹ | R² | R³ | R⁴ | X |
|---|---|---|---|---|---|
| 518 | —CH₂—C₆H₅ | —CH₂CF₃ | n-Pr | —CH₂OH | N |
| 519 | —CH₂—C₆H₅ | —CH₂CF₃ | n-Bu | —CH₂OH | C |
| 520 | —(CH₂)₂—C₆H₅ | —CH₂CF₃ | n-Bu | —CH₂OH | N |
| 521 | —(CH₂)₂—C₆H₅ | —CH₂CF₃ | —CH₂CF₃ | H | C |
| 522 | —(CH₂)₂—C₆H₅ | —CH₂CF₃ | —CH₂CF₃ | H | N |
| 523 | —(CH₂)₂—C₆H₅ | —CH₂CF₃ | Me | H | C |
| 524 | —(CH₂)₂—C₆H₅ | —CH₂CF₃ | Me | H | N |
| 525 | —(CH₂)₂—C₆H₅ | —CH₂CF₃ | Et | H | C |
| 526 | —(CH₂)₂—C₆H₅ | —CH₂CF₃ | Et | H | N |
| 527 | —(CH₂)₂—C₆H₅ | —CH₂CF₃ | n-Pr | H | C |
| 528 | —(CH₂)₂—C₆H₅ | —CH₂CF₃ | n-Pr | H | N |
| 529 | —(CH₂)₂—C₆H₅ | —CH₂CF₃ | n-Bu | H | C |
| 530 | —(CH₂)₂—C₆H₅ | —CH₂CF₃ | n-Bu | H | N |
| 531 | —(CH₂)₂—C₆H₅ | —CH₂CF₃ | —CH₂CF₃ | Me | C |

TABLE 1-continued
| Comp. No. | R¹ | R² | R³ | R⁴ | X |
|---|---|---|---|---|---|
| 532 | —(CH₂)₂—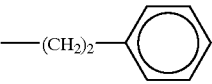 | —CH₂CF₃ | —CH₂CF₃ | Me | N |
| 533 | —(CH₂)₂—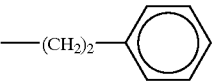 | —CH₂CF₃ | Me | Me | C |
| 534 | —(CH₂)₂—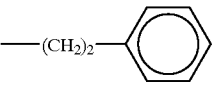 | —CH₂CF₃ | Me | Me | N |
| 535 | —(CH₂)₂—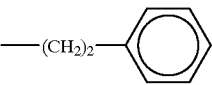 | —CH₂CF₃ | Et | Me | C |
| 536 | —(CH₂)₂—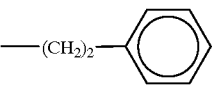 | —CH₂CF₃ | Et | Me | N |
| 537 | —(CH₂)₂—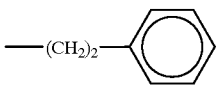 | —CH₂CF₃ | n-Pr | Me | C |
| 538 | —(CH₂)₂—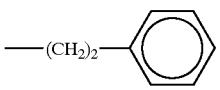 | —CH₂CF₃ | n-Pr | Me | N |
| 539 | —(CH₂)₂—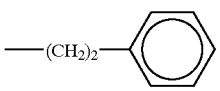 | —CH₂CF₃ | n-Bu | Me | C |
| 540 | —(CH₂)₂—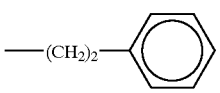 | —CH₂CF₃ | n-Bu | Me | N |
| 541 | —(CH₂)₂—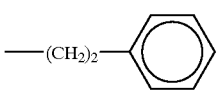 | —CH₂CF₃ | —CH₂CF₃ | —CH₂F | C |
| 542 | —(CH₂)₂—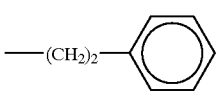 | —CH₂CF₃ | —CH₂CF₃ | —CH₂F | N |
| 543 | —(CH₂)₂—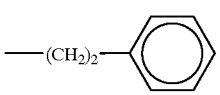 | —CH₂CF₃ | Me | —CH₂F | C |
| 544 | —(CH₂)₂—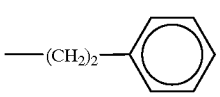 | —CH₂CF₃ | Me | CH₂F | N |
| 545 | —(CH₂)₂—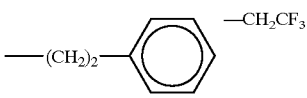 | —CH₂CF₃ | Et | —CH₂F | C |

TABLE 1-continued

| Comp. No. | R¹ | R² | R³ | R⁴ | X |
|---|---|---|---|---|---|
| 546 | —(CH$_2$)$_2$—Ph— | —CH$_2$CF$_3$ | Et | —CH$_2$F | N |
| 547 | —(CH$_2$)$_2$—Ph— | —CH$_2$CF$_3$ | n-Pr | —CH$_2$F | C |
| 548 | —(CH$_2$)$_2$—Ph— | —CH$_2$CF$_3$ | n-Pr | —CH$_2$F | N |
| 549 | —(CH$_2$)$_2$—Ph— | —CH$_2$CF$_3$ | n-Bu | —CH$_2$F | C |
| 550 | —(CH$_2$)$_2$—Ph— | —CH$_2$CF$_3$ | n-Bu | —CH$_2$F | N |
| 551 | —(CH$_2$)$_2$—Ph— | —CH$_2$CF$_3$ | CF$_3$CH$_2$— | —CH$_2$OH | C |
| 552 | —(CH$_2$)$_2$—Ph— | —CH$_2$CF$_3$ | CF$_3$CH$_2$— | —CH$_2$OH | N |
| 553 | —(CH$_2$)$_2$—Ph— | —CH$_2$CF$_3$ | Me | —CH$_2$OH | C |
| 554 | —(CH$_2$)$_2$—Ph— | —CH$_2$CF$_3$ | Me | —CH$_2$OH | N |
| 555 | —(CH$_2$)$_2$—Ph— | —CH$_2$CF$_3$ | Et | —CH$_2$OH | C |
| 556 | —(CH$_2$)$_2$—Ph— | —CH$_2$CF$_3$ | Et | —CH$_2$OH | N |
| 557 | —(CH$_2$)$_2$—Ph— | —CH$_2$CF$_3$ | n-Pr | —CH$_2$OH | C |
| 558 | —(CH$_2$)$_2$—Ph— | —CH$_2$CF$_3$ | n-Pr | —CH$_2$OH | N |
| 559 | —(CH$_2$)$_2$—Ph— | —CH$_2$CF$_3$ | n-Bu | —CH$_2$OH | C |

TABLE 1-continued

| Comp. No. | R¹ | R² | R³ | R⁴ | X |
|---|---|---|---|---|---|
| 560 | —(CH$_2$)$_2$—C$_6$H$_5$ | —CH$_2$CF$_3$ | n-Bu | —CH$_2$OH | N |

With regard to the production method of the compound of the present invention, a compound in which $R^2$ and $R^3$ of the compound of formula (I) are a $C_1$–$C_{22}$ alkyl group or an ethyl group substituted by one or more halogen atoms and $R^2=R^3$ can be synthesized, for example, in accordance with the following reaction route (1) or (2).

Reaction Route (1)

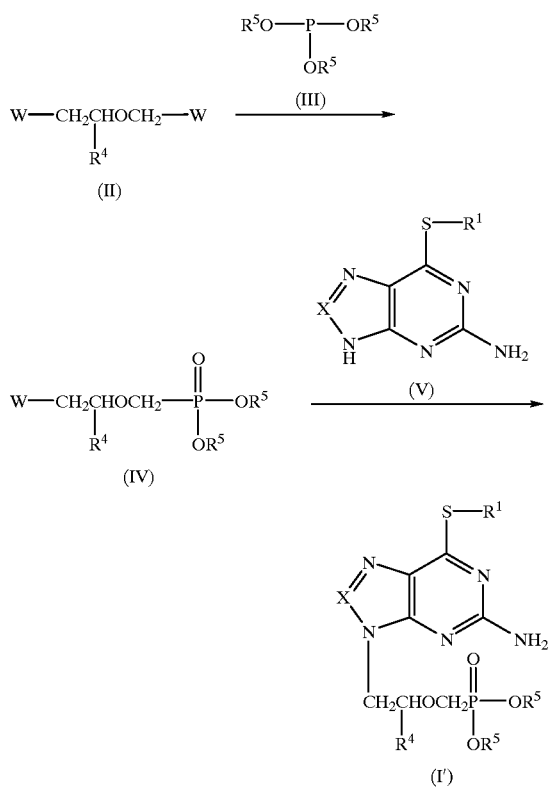

(In the above reaction formula, $R^1$, $R^4$ and X are as already defined in the foregoing, $R^5$ is a $C_1$–$C_{22}$ alkyl group or an ethyl group substituted by one or more halogen atoms and W is a leaving group such as a halogen atom, paratoluenesulfonyloxy group, methanesulfonyloxy group, trifluoromethanesulfonyloxy group or the like.)

Firstly, the compound of the aforementioned formula (II) and the compound of the aforementioned formula (III) are allowed to undergo the reaction at a temperature of from 10 to 250° C., preferably from 130 to 180° C., for a period of from 0.1 to 20 hours, preferably from 3 to 6 hours.

If necessary, the compound of the aforementioned formula (IV) obtained by the aforementioned reaction can be separated and purified by ordinary separation purification means such as distillation, adsorption, partition chromatography and the like. The compound of the aforementioned formula (IV) may be separated and purified in this manner or used as such in the following reaction without purification.

Subsequently, the compound of the aforementioned formula (IV) and the compound of the aforementioned formula (V) are allowed to react with each other at a temperature of from 10 to 200° C., preferably from 50 to 150° C., for a period of from 0.1 to 100 hours, preferably from 5 to 20 hours, in acetonitrile, tetrahydrofuran, dimethyl sulfoxide, dimethylformamide, methylpyrrolidone or the like appropriate solvent in the presence of sodium carbonate, potassium carbonate, cesium carbonate, sodium hydride, potassium hydride, triethylamine, diazabicycloundecene or the like base, thereby obtaining the compound of the aforementioned formula (I'). The thus obtained compound of the formula (I') is a compound in which $R^2$ and $R^3$ of the formula (I) are a $C_1$–$C_{22}$ alkyl group or an ethyl group substituted by one or more halogen atoms and $R^2=R^3$.

In this connection, sources of the compound of the aforementioned formula (II), the compound of the aforementioned formula (III) and the compound of the aforementioned formula (IV) to be used as starting materials of the reaction route (1) are not particularly limited, and commercially available compounds as reagents can be used or they can be optionally synthesized by known methods. In addition, the compound of the aforementioned formula (V) can be obtained from a compound of formula (VI) and a compound of formula (VIII) or a salt thereof, which will be described later, by heating them at a temperature of from 50 to 100° C. in an appropriate solvent such as acetonitrile, dimethyl sulfoxide or the like.

The compound of the aforementioned formula (I') can also be produced by the following method.

Reaction Route (2)

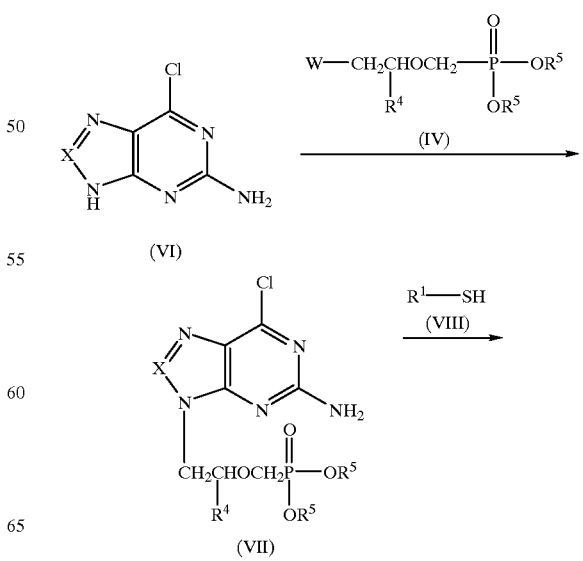

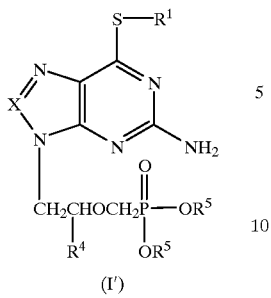

(I')

(In the above formulae, $R^1$, $R^4$, $R^5$, X and W are as defined in the foregoing.)

The compound of the aforementioned formula (VII) is obtained by allowing the compound of the aforementioned formula (IV) obtained by the reaction route (1) and the compound of the aforementioned formula (VI) to react with each other at a temperature of from 10 to 200° C., preferably from 50 to 150° C., for a period of from 0.1 to 100 hours, preferably from 5 to 20 hours, in acetonitrile, tetrahydrofuran, dimethyl sulfoxide, dimethylformamide, methylpyrrolidone or the like appropriate solvent in the presence of sodium carbonate, potassium carbonate, cesium carbonate, sodium hydride, potassium hydride, triethylamine, diazabicycloundecene or the like base. Thereafter, the compound of the aforementioned formula (I') can be obtained by allowing the compound of the aforementioned formula (VII) and a mercaptan represented by the compound of the aforementioned formula (VIII) or a salt thereof (for example, sodium salt, potassium salt, lithium salt, triethylamine salt or the like) to react with each other at a temperature of from 10 to 200° C., preferably from 70 to 120° C., for a period of from 0.1 to 100 hours, preferably from 5 to 12 hours, in an appropriate solvent such as acetonitrile, tetrahydrofuran, dimethyl sulfoxide, dimethylformamide, methylpyrrolidone or the like, if necessary in the presence of an appropriate tertiary amine.

In this connection, source of the compound of the aforementioned formula (VI) to be used as material of the reaction route (2) is not particularly limited, and commercially available compound as a reagent can be used or it can be optionally synthesized by known methods.

The compound of the aforementioned formula (I') can also be produced by the following method.

Reaction Route (3)

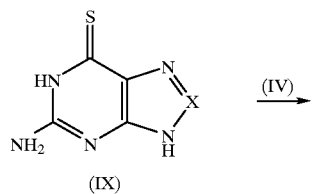

(IX)

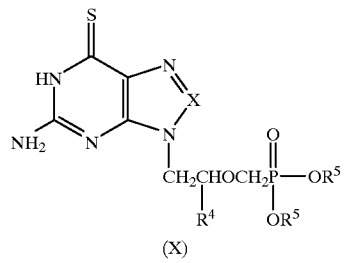

(X)

(In the above formulae, $R^1$, $R^4$, $R^5$, X and W are as defined in the foregoing, and Y is a halogen atom such as chlorine atom, bromine atom, iodine atom or the like, or mesyloxy group or tosyloxy group.)

The compound of the aforementioned formula (X) is obtained by allowing the compound of the aforementioned formula (IV) obtained by the reaction route (1) and the compound of the aforementioned formula (IX) to react with each other at a temperature of from 10 to 200° C., preferably from 50 to 150° C., for a period of from 0.1 to 100 hours, preferably from 5 to 20 hours, in acetonitrile, tetrahydrofuran, dimethyl sulfoxide, dimethylformamide, methylpyrrolidone or the like appropriate solvent in the presence of sodium carbonate, potassium carbonate, cesium carbonate, sodium hydride, potassium hydride, triethylamine, diazabicycloundecene or the like base. Thereafter, the compound of the aforementioned formula (I') is obtained by allowing the compound of the aforementioned formula (X) and the alkyl halide, alkyl mesylate or alkyl tosylate compound represented by the aforementioned formula (XI) to react with each other at a temperature of from 10 to 200° C., preferably from 50 to 150° C., for a period of from 0.1 to 100 hours, preferably from 1 to 20 hours, in acetonitrile, tetrahydrofuran, dimethyl sulfoxide, dimethylformamide, methylpyrrolidone or the like appropriate solvent in the presence of sodium carbonate, potassium carbonate, cesium carbonate, sodium hydride, potassium hydride, triethylamine, diazabicycloundecene or the like base.

The compound of the aforementioned formula (X) can also be produced by the following method.

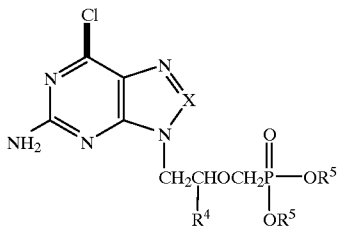

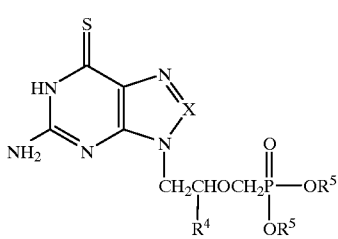

(In the above formulae, $R^4$, $R^5$ and X are as defined in the foregoing.)

The compound of the aforementioned formula (X) is obtained by allowing the compound of the aforementioned formula (VII) obtained by the reaction route (2) to undergo the reaction in the presence of thiourea or the like at a temperature of from 10 to 200° C., preferably from 50 to 150° C., for a period of from 0.1 to 100 hours, preferably from 0.25 to 4 hours, in an appropriate solvent such as acetonitrile, tetrahydrofuran, dimethyl sulfoxide, dimethylformamide, methylpyrrolidone, ethanol, methanol, 2,2,2-trifluoroethanol or the like.

In this connection, source of the compound of the aforementioned formula (IX) to be used as material of the reaction route (3) is not particularly limited, and commercially available compound as a reagent can be used or it can be optionally synthesized by known methods.

A compound of the formula (I) having a substituent group other than $R^5$ of the compound of the aforementioned formula (I') can be obtained by further carrying out reaction of the compound of formula (I').

A compound of the formula (I) in which $R^3$ is hydrogen atom, a $C_1$–$C_{22}$ alkyl group, an acylthioethyl group or an ethyl group substituted by one or more halogen atoms and $R^2$ is a $C_1$–$C_4$ alkyl group or an ethyl group substituted by one or more halogen atoms is obtained by allowing the compound of the aforementioned formula (I') to react with a compound of formula (XII):

$$R^6OH \quad (XII)$$

(wherein $R^6$ is hydrogen atom, a $C_1$–$C_4$ alkyl group, an acylthioethyl group or an ethyl group substituted by one or more halogen atoms) at a temperature of from 10 to 100° C., preferably from 20 to 30° C., for a period of from 0.1 to 100 hours, preferably from 5 to 12 hours, without solvent or in an appropriate solvent such as dichloromethane or the like chlorine solvent, pyridine, acetonitrile, tetrahydrofuran, dimethyl sulfoxide, dimethylformamide, methylpyrrolidone or the like, if necessary in the presence of p-toluenesulfonic acid, methanesulfonic acid, hydrochloric acid, phosphoric acid or the like acid.

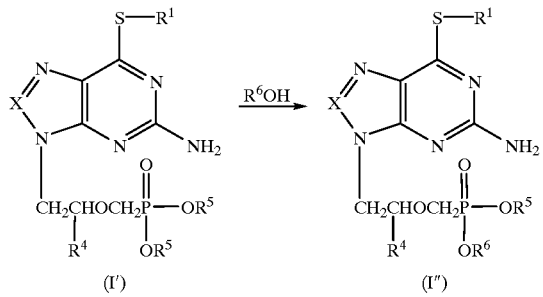

(In the above formulae, $R^1$, $R^4$, $R^5$, $R^6$ and X are as defined in the foregoing.)

A compound of the formula (I) in which $R^2$ and $R^3$ are each independently a $C_1$–$C_{22}$ alkyl group, an acylthioethyl group or an ethyl group substituted by one or more halogen atoms can also be obtained by the following method.

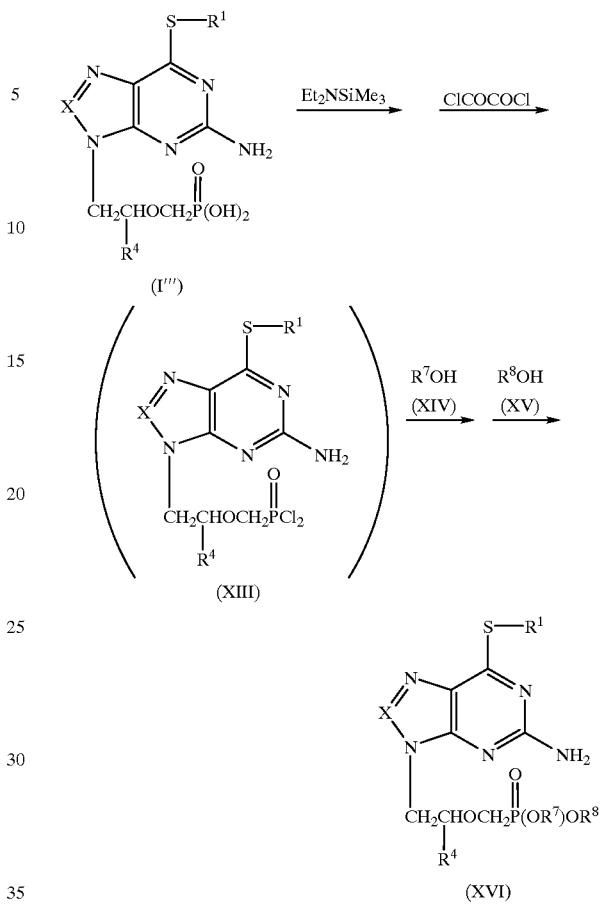

(In the above formulae, $R^1$, $R^4$ and X are as defined in the foregoing, and $R^7$ or $R^8$ is each independently hydrogen atom, a $C_1$–$C_{22}$ alkyl group, an acylthioethyl group or an ethyl group substituted by one or more halogen atoms.)

Firstly, a compound of the aforementioned formula (I''') obtained by hydrolyzing the compound (I') is allowed to react with trimethylsilyldiethylamine in an appropriate solvent such as dichloromethane, dichloroethane, chloroform or the like chlorine solvent at around room temperature for about 1 hour. In this case, trimethylsilyldiethylamine is used in an amount of 2 moles or more based on 1 mole of the compound of the aforementioned formula (II''').

Next, the reaction solution is concentrated to dryness, the resulting residue is dissolved in an appropriate solvent such as dichloromethane or the like chlorine solvent, oxalyl chloride is added to the solution in an amount of 2 moles or more based on 1 mole of the compound of the aforementioned formula (I'''), and then the mixture is allowed to undergo the reaction in the presence of a catalytically effective amount of dimethylfornamide for about 1 hour in an ice bath and then about 1 hour at around room temperature.

After evaporation of the solvent, the thus obtained compound of the aforementioned formula (XIII) is allowed to react, generally without purification, with the compound of formula (XIV) and/or the compound of formula (XV) at a temperature of from 10 to 100° C., preferably from 20 to 30° C., for a period of from 0.1 to 100 hours, preferably from 5 to 12 hours, in an appropriate solvent such as dichloromethane or the like chlorine solvent, pyridine, acetonitrile, tetrahydrofuran, dimethyl sulfoxide, dimethylformamide, methylpyrrolidone. The thus obtained compound of the formula (XVI) is a compound in which $R^2$ and $R^3$ of the compound of formula (I) are each independently hydrogen atom, a $C_1$–$C_{22}$ alkyl group, an acylthioethyl group or an ethyl group substituted by one or more halogen atoms.

In this connection, the compound of the aforementioned formula (I''') to be used as material of the aforementioned reaction can be obtained by hydrolyzing the compound of formula (I'), but it can be obtained more efficiently by preparing the compound of formula (I') from a compound of the aforementioned formula (IV) in which $R^5$ is a $C_1$–$C_4$ alkyl group and then allowing the thus prepared compound to react with triethyliodosilane, trimethyibromosilane or the like compound.

A compound in which $R^2$ and $R^3$ of the compound of formula (I) are an acyloxymethyl group or a compound in which one of them is an acyloxymethyl group and the other is hydrogen atom is obtained by allowing the compound of the aforementioned formula (I''') to react with an acyloxymethyl halide compound represented by formula (XVII):

$$R^9Y \quad\quad (XVII)$$

(wherein $R^9$ is an acyloxymethyl group and Y is a halogen atom such as chlorine atom, bromine atom, iodine atom or the like) at a temperature of from 0 to 200° C., preferably from 10 to 100° C., for a period of from 1 to 300 hours, preferably from 10 to 200 hours, inacetonitrile, tetrahydrofuran, dimethyl sulfoxide, dimethylformamide, methylpyrrolidone or the like appropriate solvent in the presence of sodium carbonate, potassium carbonate, cesium carbonate, sodium hydride, potassium hydride, triethylamine, pyridine, diazabicycloundecene, N,N'-dichlorohexyl-4-morpholine carboxyamidine or the like base.

When both of $R^2$ and $R^3$ of the compound of interest are an acyloxymethyl group, 2 moles of the compound of the formula (XVII) may be allowed to react with 1 mole of the compound of formula (I'''), or at the same molar ratio when one of them is an acyloxymethyl group.

Also, when one of $R^2$ and $R^3$ is an acyloxymethyl group and the other is a $C_1$–$C_{22}$ alkyl group, an acylthioethyl group or an ethyl group substituted by one or more halogen atoms, such a compound can be produced by firstly preparing a compound (I'') in which one of $R^2$ and $R^3$ is a $C_1$–$C_{22}$ alkyl group, an acylthioethyl group or an ethyl group substituted by one or more halogen atoms and the other is hydrogen atom (with the proviso that $R^6$ is hydrogen atom) and then allowing the thus prepared compound to react with the compound of formula (XVII) in accordance with the aforementioned method.

As occasion demands, the compound of the aforementioned formula (I) obtained in these manners may be separated and purified from the reaction solution by optionally selecting ordinary nucleotide separation purification means such as recrystallization, adsorption, ion exchange, partition chromatography or the like.

It is expected that the compound of the present invention can be used as an antiviral agent as will be described later in Test Examples and has antitumor activity as can be found in other ionic phosphonate nucleotide analogs. Though not particularly limited, illustrative examples of the virus to be treated include RNA viruses such as human immunodeficiency virus, influenza virus, hepatitis C virus and the like and DNA viruses such as herpes simplex virus I, herpes simplex virus II, cytomegalovirus, varicella zoster virus, hepatitis B virus and the like, of which hepatitis B virus is most desirable.

When the compound of the present invention is used as a medicament, it is administered alone or as a pharmaceutical composition in combination with a pharmacologically acceptable carrier. The composition is decided based on the solubility, chemical characteristics, route of administration, dosage regimen and the like of the compound. For example, it can be administered orally as granules, fine subtilaes, powders, tablets, hardsyrups, soft capsules, troches, syrups, emulsions, soft gelatin capsules, gels, pastes, suspensions, liposomes and the like dosage forms or intravenously, intramuscularly or percutaneously as injections. It can also be used as powders for injection use which are dissolved before using.

The pharmacologically acceptable carrier is an organic or inorganic solid or liquid for medical use which is suitable for oral, rectal, parenteral or topical administration. Examples of the solid carrier to be used in producing solid preparations include lactose, sucrose, starch, talc, cellulose, dextrin, kaolin, calciumcarbonate, agar, pectin, stearic acid, magnesium stearate, lecithin, sodium chloride and the like. Examples of the liquid carrier to be used in producing liquid preparations for oral administration use include glycerol, peanut oil, polyvinyl pyrrolidone, olive oil, ethanol, benzyl alcohol, propylene glycol, physiological saline, water and the like. In addition to the just described carriers, these preparations can contain auxiliary substances such as moistening agents, suspending agents, sweeteners, aromatics, coloring agents, preservatives and the like. Also, the liquid preparation may be used by containing it in capsules made of an absorbable material such as gelatin.

Examples of the solvent or suspending agent to be used in producing injections and the like preparations for parenteral administration use include water, propylene glycol, polyethylene glycol, benzyl alcohol, ethyl oleate, lecithin and the like.

Since compounds of the present invention, particularly the ester derivatives represented by the aforementioned formula (I'), have high oral absorption ability as will be shown later in Test Examples, it is desirable according to the present invention to administer them in the form of oral preparations. In this connection, each of the aforementioned pharmaceutical preparations can be prepared in the ordinary method.

When used by oral administration, the clinical dose is generally from 1 to 500 mg/kg, preferably from 5 to 50 mg/kg, per day per adult as the compound of the present invention, but the administration may be carried out by optionally changing the dose depending on the age, morbid state, symptoms, the presence or absence of simultaneous administration and the like. The just described daily dose of the compound of the present invention may be used once a day or by dividing the daily dose into 2 to several doses per day at appropriate intervals or by intermittent administration.

When used as injections, the clinical dose is generally from 0.1 to 50 mg/kg, preferably from 0.1 to 5 mg/kg, per day per adult as the compound of the present invention.

EXAMPLES

Examples of the present invention are given below by way of illustration and not by way of illustration.

Inventive Example 1

Production of 2-amino-9-[2-[bis(2,2,2-trifluoroethyl) phosphonylmethoxy]ethyl]-6-ethylthiopurine (Compound No. 2 in Table 1)

An 87 g (670 mmol) portion of 2-chloroethylchloromethyl ether and 200 g (610 mmol) of tris(2,2,2-trifluoroethyl) phosphite were allowed to react with each other at 160° C. for 7 hours, thereby obtaining 2-[bis(2,2,2-trifluoroethyl)phosphonylmethoxy]ethyl chloride quantitatively.

A 206 g portion of 2-[bis(2,2,2-trifluoroethyl) phosphonylmethoxy]ethyl chloride was dissolved in 2,000 ml of methyl ethyl ketone and heated under reflux for 8 hours together with 270 g of sodium iodide. After the reaction, this was cooled down to room temperature and then concentrated to dryness. The resulting residue was dissolved in chloroform/hexane, allowed to be adsorbed by a silica gel column and then eluted with chloroform/hexane, thereby obtaining 2-[bis(2,2,2-trifluoroethyl)phosphonylmethoxy] ethyl iodide quantitatively.

A 15.0 g (88 mmol) portion of 2-amino-6-chloropurine was suspended in 360 ml of dimethylformamide and allowed to react with 13.9 ml (93 mmol) of 1,8-diazabicyclo [5.4.0]undec-7-ene at 80° C. for 1 hour. Next, 23.8 ml of 2-[bis(2,2,2-trifluoroethyl)phosphonylmethoxy]ethyl iodide was added to the reaction solution to carry out 5 hours of reaction at 100° C. After the reaction, this was cooled down to room temperature and then concentrated to dryness. The resulting residue was dissolved in chloroform, allowed to be adsorbed by a silica gel column and then eluted with 5% methanol-chloroform to obtain 23.3 g (56%) of 2-amino-9-[2-[bis(2,2,2-trifluoroethyl)phosphonylmethoxy]ethyl]-6-chloropurine.

An 8.0 g portion of sodium thioethoxide was added to 400 ml of dimethylformamide solution containing 47.1 g of 2-amino-9-[2-[bis(2,2,2-trifluoroethyl)phosphonylmethoxy] ethyl]-6-chloropurine, and the mixture was stirred at 80° C. for 30 minutes. The reaction mixture was cooled down to room temperature and then concentrated to dryness. The resulting residue was dissolved in chloroform, allowed to be adsorbed by a silica gel column and then eluted with 0.4% to 1.2% methanol-chloroform to obtain 14.3 g (30%) of 2-amino-9-[2-[bis(2,2,2-trifluoroethyl)phosphonylmethoxy] ethyl]-6-ethylthiopurine.

UV: λmax=248, 322 (0.01 N HCl/CH$_3$OH); λmax=245, 309 (0.01 N NaOH/CH$_3$OH); $^1$H-NMR (CDCl$_3$, δ): 1.41 (t, J=7.3 Hz, 3 H), 3.30 (q, J=7.4 Hz, 2 H), 3.88–3.98 (m, 4 H), 4.20–4.48 (m, 6 H), 4.88 (bs, 2 H), 7.68 (s, 1 H).

Inventive Example 2
Production of 2-amino-9-[2-[bis(2,2,2-trifluoroethyl) phosphonylmethoxy]ethyl]-6-methylthiopurine (Compound No. 1 in Table 1)
The title compound was obtained by repeating the procedure of Inventive Example 1, except that sodium thiomethoxide was used instead of sodium thioethoxide.

UV: λmax=248, 322 (0.01 N HCl/ CH$_3$OH); λmax=245, 309 (0.01 N NaOH/CH$_3$OH); $^1$H-NMR (CDCl$_3$, δ): 2.64 (s, 3 H), 3.88–4.00 (m, 4 H), 4.27 (t, J=5.0 Hz, 2 H), 4.37 (septet, J=8.3 Hz, 4 H), 4.89 (s, 2 H), 7.69 (s, 1 H).

Inventive Example 3
Production of 9-[2-[bis(2,2,2-trifluoroethyl) phosphonylmethoxy]ethyl]-6-benzylthioguanine (Compound No. 481 in Table 1)
The title compound was obtained by repeating the procedure of Inventive Example 1, except that benzylmercaptan and triethylamine were used in stead of sodium thioethoxide.

UV: λmax=248, 322 (0.01 N HCl/CH$_3$OH); λmax=245, 309 (0.01 N NaOH/CH$_3$OH); $^1$H-NMR (CDCl$_3$, δ): 3.86–3.96 (m, 4 H), 4.20–4.48 (m, 6 H), 4.57 (s, 2 H), 4.91 (bs, 2 H), 7.20–7.50 (m, 5 H), 7.68 (s, 1 H).

Inventive Example 4
Production of 2-amino-9-[2-[bis(2,2,2-trifluoroethyl) phosphonylmethoxy]ethyl]-6-n-butylthiopurine (Compound No. 5 in Table 1)

The title compound was obtained by repeating the procedure of Inventive Example 1, except that n-butanethiol and triethylamine were used in stead of sodium thioethoxide.

UV: λmax=248, 322 (0.01 N HCl/CH$_3$OH); λmax=245, 309 (0.01 N NaOH/CH$_3$OH); $^1$H-NMR (CDCl$_3$, δ): 0.95 (t, J=7.3 Hz, 3 H), 1.40–1.60 (m, 2 H), 1.68–1.84 (m, 2 H), 3.30 (t, J=7.1 Hz, 2 H), 3.84–4.05 (m, 4 H), 4.18–4.50 (m, 6 H), 4.88 (s, 2 H), 7.68 (s, 1 H).

Inventive Example 5
Production of 2-amino-9-[2-[bis(2,2,2-trifluoroethyl) phosphonylmethoxy]ethyl]-6-i-butylthiopurine (Compound No. 6 in Table 1)
The title compound was obtained by repeating the procedure of Inventive Example 1, except that i-butanethiol and triethylamine were used in stead of sodium thioethoxide.

UV: λmax=248, 322 (0.01 N HCl/CH$_3$OH); λmax=245, 309 (0.01 N NaOH/CH$_3$OH); $^1$H-NMR (CDCl$_3$, δ): 1.06 (d, J=6.7 Hz, 6 H), 2.00 (apparent septet, J=6.7 Hz, 1 H), 3.22 (d, J=6.8 Hz, 2 H), 3.84–4.03 (m, 4 H), 4.20–4.47 (m, 6 H), 4.86 (s, 2 H), 7.68 (s, 1 H).

Inventive Example 6
Production of 2-amino-9-[2-[bis(2,2,2-trifluoroethyl) phosphonylmethoxy]ethyl]-6-n-hexylthiopurine (Compound No. 10 in Table 1)
The title compound was obtained by repeating the procedure of Inventive Example 1, except that n-hexanethiol and triethylamine were used in stead of sodium thioethoxide.

UV: λmax=248, 322 (0.01 N HCl/CH$_3$OH); λmax=245, 309 (0.01 N NaOH/CH$_3$OH); $^1$H-NM (CDCl$_3$, δ): 0.89 (t, J=6.9 Hz, 3 H), 1.22–1.58 (m, 6 H), 1.67–1.82 (m, 2 H), 3.29 (t, J=7.2 Hz, 2 H), 3.86–4.00 (m, 4 H), 4.20–4.48 (m, 6 H), 4.86 (bs, 2 H), 7.68 (s, 1 H).

Inventive Example 7
Production of 2-amino-9-[2-[bis(2,2,2-trifluoroethyl) phosphonylmethoxy]ethyl]-6-n-propylthiopurine (Compound No. 3 in Table 1)
The title compound was obtained by repeating the procedure of Inventive Example 1, except that n-propanethiol and triethylamine were used in stead of sodium thioethoxide.

UV: λmax=248, 322 (0.01 N HCl/CH$_3$OH); λmax=245, 309 (0.01 N NaOH/CH$_3$OH); $^1$H-NMR (CDCl$_3$, δ): 1.06 (t, J=7.2 Hz, 3 H), 1.78 (q, J=7.2 Hz, 2 H), 3.28 (t, J=7.0 Hz, 2 H), 3.84–3.98 (m, 4 H), 4.23–4.45 (m, 6 H), 4.87 (bs, 2 H), 7.68 (s, 1 H).

Inventive Example 8
Production of 2-amino-9-[2-[bis(2,2,2-trifluoroethyl) phosphonylmethoxy]ethyl]-6-i-propylthiopurine (Compound No. 4 in Table 1)
The title compound was obtained by repeating the procedure of Inventive Example 1, except that i-propanethiol and triethylamine were used in stead of sodium thioethoxide.

UV: λmax=248, 322 (0.01 N HCl/CH$_3$OH); λmax=245, 309 (0.01 N NaOH/CH$_3$OH); $^1$H-NMR (CDCl$_3$, δ): 1.45 (d, J=6.9 Hz, 6 H), 3.86–3.98 (m, 4 H), 4.20–4.46 (m, 7 H), 4.86 (bs, 2 H), 7.67 (s, 1 H).

Inventive Example 9
Production of 2-amino-9-[2-[sodium (2,2,2-trifluoroethyl) phosphonylmethoxy]ethyl]-6-ethylthiopurine
A 0.71 ml portion of 1 N sodium hydroxide aqueous solution was added to 2.6 ml of THF solution containing 334 mg of 2-amino-9-[2-[bis(2,2,2-trifluoroethyl) phosphonylmethoxy]ethyl]-6-ethylthiopurine, and the mixture was stirred at room temperature for 3 hours and then freeze-dried to obtain 257 mg (89%) of the title compound.

UV: $\lambda$max=248, 322 (0.01 N HCl/CH$_3$OH); $\lambda$max=245, 309 (0.01 N NaOH/CH$_3$OH); $^1$H-NMR (D$_2$O, $\delta$): 1.38 (t, J=7.4 Hz, 3 H), 3.26 (q, J=7.4 Hz, 2 H), 3.69 (q, J=8.8 Hz, 2 H), 3.85–4.07 (m, 4 H), 4.31 (t, J=5.0 Hz, 2 H), 7.99 (s, 1 H).

Inventive Example 10

Production of 2-amino-9-[2-[bis(2,2,2-trifluoroethyl) phosphonylmethoxy]ethyl]-6-ethylthiopurine. 2HCl (Compound No. 2 in Table 1)

An 8 ml portion of ethyl acetate solution containing 763 mg of 2-amino-9-[2-[bis(2,2,2-trifluoroethyl) phosphonylmethoxy]ethyl]-6-ethylthiopurine was added dropwise to 2 ml of saturated hydrogen chloride/ethyl acetate solution, the mixture was stirred at room temperature for 30 minutes and concentrated under a reduced pressure and then the thus precipitated crystals were washed with ethyl acetate and dried to obtain 747 mg (99%) of the title compound.

UV: $\lambda$max=248, 322 (0.01 N HCl/CH$_3$OH); $\lambda$max=245, 309 (0.01 N NaOH/CH$_3$OH); $^1$H-NMR (DMSO-d$_6$, $\delta$): 1.32 (t, J=7.3 Hz, 3 H), 3.30 (q, J=7.3 Hz, 2 H), 3.80–3.94 (m, 2 H), 4.13 (d, J=7.9 Hz, 2 H), 4.22–4.30 (m, 2 H), 4.53–4.77 (m, 4 H), 8.21 (s, 1 H).

Inventive Example 11

Production of 2-amino-9-[2-(diethylphosphonylmethoxy) ethyl]-6-ethylthiopurine

The title compound was obtained by repeating the procedure of Inventive Example 1, except that triethyl phosphite was used in stead of (2,2,2-trifluoroethyl) phosphite.

$^1$H-NMR (CDCl$_3$, $\delta$): 1.30 (t, J=7.0 Hz, 3 H), 1.42 (t, J=7.4 Hz, 3 H), 3.31 (q, J=7.5 Hz, 2 H), 3.77 (d, J=8.3 Hz, 2 H), 3.89 (t, J=5.0 Hz, 2 H), 4.09 (quintet, J=7.4 Hz, 4 H), 4.26 (t, J=5.0 Hz, 2 H), 4.87 (bs, 2 H), 7.75 (s, 1 H).

Test Example 1

Hepatitis B virus (HBV) growth inhibition effect

HBV growth inhibition effect was measured in accordance with a known method (K. Ueda et al., *Virology*, 169, 213–216 (1989)).

A total of 2×10$^4$ cells of HB611 (a HBV-producing recombinant human hepatoma cell strain) were cultured at 37° C. in Dulbecco's ME medium containing 10% fetal bovine serum, streptomycin (100 $\mu$g/ml), penicillin (100 IU/ml) and Geneticin (trade name, an antibiotic substance manufactured by Life Technologies) (0.2 mg/ml). The medium was exchanged on the 2nd and 5th days of the culturing and then replaced by the medium supplemented with a sample to be tested at a final concentration of from 0.005 to 100 $\mu$M after 8, 11 and 14 days of the culturing, and DNA was recovered from the cells after 17 days of the culturing. The amount of HBV-DNA in the cells was measured by Southern blotting to calculate concentration of the compound to give 50% inhibition of HBV-DNA synthesis. Also, the concentration of each compound required for causing death to 50% of the HB611 cells was calculated. For the sake of comparison, the same test was carried out on a known compound PMFA, a dipivaloyloxymethyl ester of PMEA (Reference Example 1) and a known compound 9-[2-[bis(2,2,2-trifluoroethyl)-phosphonylmethoxy]ethyl]-2-amino-6-p-toluylthiopurine disclosed in EP 632048 (Reference Example 2). The results are shown in Table 2 below. In this connection, the compound No. corresponds to the compound No. in Table 1.

TABLE 2

| Compound No. | 50% inhibitory concentration for HBV-DNA synthesis ($\mu$M) | 50% Cytotoxic concentration for HB611 cells ($\mu$M) |
| --- | --- | --- |
| 2 | 0.06 | >1000 |
| 3 | 0.02 | >1000 |
| 4 | 0.07 | >1000 |
| PMEA | 0.3 | 334 |
| Ref. Ex. 1 | 1.08 | 17.7 |
| Ref. Ex. 2 | 0.06 | 108 |

Test Example 2

Inhibitory effect on HBV replication of low molecular weight fraction prepared from liver homogenate of a mouse that was orally administered with a compound.

A sample to be tested was orally administered to each mouse of three animals per group in a dose of 0.2 g/kg, liver perfusion was carried out from the portal vein one hour after the administration and then the liver was excised. The thus excised liver was mixed with the same weight of physiological saline and was homogenized, and then a sample of low molecular weight fraction of the homogenate was prepared using an ultrafiltration membrane having a cutoff of 5,000 molecular weight.

A total of 2×10$^4$ cells of HB611 were cultured at 37° C. in Dulbecco's ME medium containing 10% fetal bovine serum, streptomycin (100 $\mu$g/ml), penicillin (100 IU/ml) and Geneticin (0.2 mg/ml). The medium was exchanged on the 2nd and 5th days of the culturing and then replaced by the medium supplemented with 1% of the just described low molecular weight fraction sample after 8, 11 and 14 days of the culturing, and DNA was recovered from the cells after 17 days of the culturing. The amount of HBV-DNA in the cells was measured by Southern blotting to evaluate inhibitory effect on HBV-DNA synthesis in the cells. For the sake of comparison, the same test was carried out on 2-amino-9-(2-phosphonylmethoxyethyl)-6-n-propylthiopurine (Reference Example 3) as a typical example of the compounds disclosed in U.S. Pat. No. 7,683,432.

TABLE 3

| Compound No. | % inhibition of HBV-DNA synthesis |
| --- | --- |
| 3 | 49 |
| Ref. Ex. 3 | 17 |

INDUSTRIAL APPLICABILITY

Since the phosphonate nucleotide derivatives of the present invention have excellent antiviral activity, show high oral absorption ability and are also excellent in terms of their distribution into hepatic cells, their usefulness as medicaments is expected.

What is claimed is:

1. A phosphate nucleotide compound represented by formula (I)

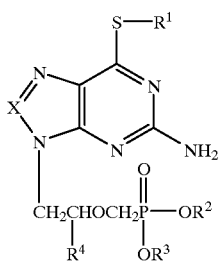

(in the above formula (I), $R^1$ represents a $C_1$–$C_6$ alkyl group or a $C_7$–$C_{10}$ aralkyl group, each of $R^2$ and $R^3$ independently represents a hydrogen atom (with the proviso that $R^2$ and $R^3$ are not hydrogen atoms at the same time), a $C_1$–$C_{22}$ alkyl group, an alkylcarbonyloxymethyl group, having 3 to 10 carbon atoms an alkylcarbonylthioethyl group having 4 to 11 carbon atoms or an ethyl group substituted by one or more halogen atoms, $R^4$ represents a hydrogen atom, a $C_1$–$C_4$ alkyl group, a $C_1$–$C_4$ hydroxyalkyl or a $C_1$–$C_4$ alkyl group substituted by one or more halogen atoms and X represents a carbon atom or a nitrogen atom), a salt thereof, a hydrate thereof or a solvate thereof.

2. A phosphonate nucleotide compound represented by formula (I):

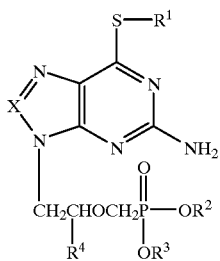

(I)

(in the above formula (I), $R^1$ represents a $C_1$–$C_6$ alkyl group and each of $R^2$ and $R^3$ independently represents an ethyl group substituted by one or more halogen atoms, $R^4$ represents a hydrogen atom, a $C_1$–C4 alkyl group, a $C_1$–$C_4$ hydroxyalkyl group or a $C_1$–$C_4$ alkyl group substituted by one or more halogen atoms and X represents a carbon atom or a nitrogen atom), a salt thereof, a hydrate thereof or a solvate thereof.

3. A phosphonate nucleotide compound represented by formula (I):

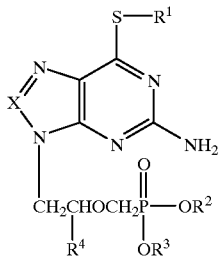

(I)

(in the above formula (I), $R^1$ represents a $C_1$–$C_6$ alkyl group and each of $R^2$ and $R^3$ is a 2,2,2-trifluoroethyl group, $R^4$ represents a hydrogen atom, a $C_1$–$C_4$ alkyl group, a $C_1$–$C_4$ hydroxyalkyl group or a $C_1$–$C_4$ alkyl group substituted by one or more halogen atoms and X represents a carbon atom or a nitrogen atom), a salt thereof, a hydrate thereof or a solvate thereof.

4. A phosphonate nucleotide compound represented by formula (I):

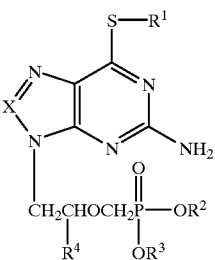

(I)

(in the above formula (I), $R^1$ represents a $C_1$–$C_6$ alkyl group or a $C_7$–$C_{10}$ aralkyl group, each of $R^2$ and $R^3$ independently represents a hydrogen atom (with the proviso that $R^2$ and $R^3$ are not hydrogen atoms at the same time), a $C_1$–$C_{22}$ alkyl group, an acyloxymethyl group, an acylthioethyl group or an ethyl group substituted by one or more halogen atoms, $R^4$ represents a hydrogen atom, a $C_1$–$C_4$ alkyl group, a $C_1$–$C_4$ hydroxyalkyl group or a $C_1$–$C_4$ alkyl group substituted by one or more halogen atoms and X represents a carbon atom or a nitrogen atom), a salt thereof, a hydrate thereof or a solvate thereof wherein the acyloxymethyl group of $R^2$ and $R^3$ is an acetyloxymethyl, propionyloxymethyl, butyryloxymethyl, isobutyryloxymethyl, valeryloxymethyl, isovaleryloxymethyl or pivaloyloxymethyl group and the acylthioethyl group of $R^2$ and $R^3$ is an acetylthioethyl, propionylthioethyl, butyrylthioethyl, isobutyrylthioethyl, valerythioethyl, isovalerythioethyl or pivaloylthioethyl group.

5. A pharmaceutical composition which comprises any one of the compounds described in claim 1 and a pharmacologically acceptable carrier.

6. A pharmaceutical composition comprising a phosphonate nucleotide compound represented by formula (I):

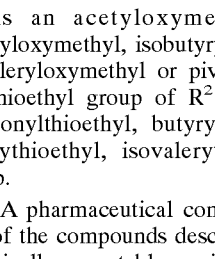

(I)

(in the above formula (I), $R^1$ represents a $C_1$–$C_6$ alkyl group and each of $R^2$ and $R^3$ independently represents an ethyl group substituted by one or more halogen atoms, $R^4$ represents a hydrogen atom, a $C_1$–$C_4$ alkyl group, a $C_1$–$C_4$ hydroxyalkyl group or a $C_1$–$C_4$ alkyl group substituted by one or more halogen atoms and X represents a carbon atom or a nitrogen atom), a salt thereof, a hydrate thereof or a solvate thereof and a pharmaceutical carrier.

7. A pharmaceutical composition comprising a phosphonate nucleotide compound represented by formula (I):

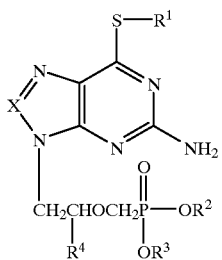

(in the above formula (I), $R^1$ represents a $C_1$–$C_6$ alkyl group and each of $R^2$ and $R^3$ is a 2,2,2-trifluoroethyl group, $R^4$ represents a hydrogen atom, a $C_1$–$C_4$ alkyl group, a $C_1$–$C_4$ hydroxyalkyl group or a $C_1$–$C_4$ alkyl group substituted by one or more halogen atoms and X represents a carbon atom or a nitrogen atom), a salt thereof, a hydrate thereof or a solvate thereof and a pharmaceutically acceptable carrier.

8. A pharmaceutical composition comprising a phosphonate nucleotide compound represented by formula (I):

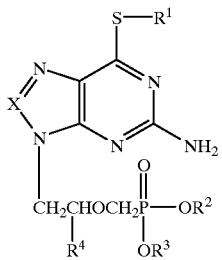

(in the above formula (I), $R^1$ represents a $C_1$–$C_6$ alkyl group or a $C_7$–$C_{10}$ aralkyl group, each of $R^2$ and $R^3$ independently represents a hydrogen atom (with the proviso that $R^2$ and $R^3$ are not hydrogen atoms at the same time), a $C_1$–$C_{22}$ alkyl group, an acyloxymethyl group, an acylthioethyl group or an ethyl group substituted by one or more halogen atoms, $R^4$ represents a hydrogen atom, a $C_1$–$C_4$ alkyl group, a $C_1$–$C_4$ hydroxyalkyl group or a $C_1$–$C_4$ alkyl group substituted by one or more halogen atoms and X represents a carbon atom or a nitrogen atom), a salt thereof, a hydrate thereof or a solvate thereof and a pharmaceutical carrier, wherein the acyloxymethyl group of $R^2$ and $R^3$ is an acetyloxymethyl, propionyloxymethyl, butyryloxymethyl, isobutyryloxymethyl, valeryloxymethyl, isovaleryloxymethyl or pivaloyloxymethyl group and the acylthioethyl group of $R^2$ and $R^3$ is an acetylthioethyl, propionylthioethyl, butyrylthioethyl, isobutyrylthioethyl, valerythioethyl, isovalerythioethyl or pivaloylthioethyl group.

9. A method for the treatment of a hepatitis B virus (HBV) infection which comprises administering to a patient in need of such treatment an effective amount of a substance selected from the group consisting of the phosphonate nucleotide compound, a salt thereof a hydrate thereof and a solvate thereof as defined in claim 1.

10. A method for the treatment of a hepatitis B virus (HBV) infection which comprises administering to a patient in need of such treatment an effective amount of a substance selected from the group consisting of the phosphonate nucleotide compound, a salt thereof a hydrate thereof and a sovate thereof wherein the phosphonate nucleotide compound is represented by formula (I):

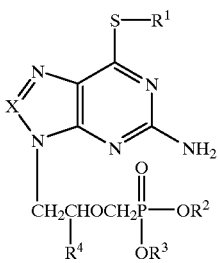

(in the above formula (I), $R^1$ represents a $C_1$–$C_6$ alkyl group or a $C_7$–$C_{10}$ aralkyl group, each of $R^2$ and $R^3$ independently represents a hydrogen atom (with the proviso that $R^2$ and $R^3$ are not hydrogen atoms at the same time), a $C_1$–$C_{22}$ alkyl group, an acyloxymethyl group, an acylthioethyl group or an ethyl group substituted by one or more halogen atoms, $R^4$ represents a hydrogen atom, a $C_1$–$C_4$ alkyl group, a $C_1$–$C_4$ hydroxyalkyl group or a $C_1$–$C_4$ alkyl group substituted by one or more halogen atoms and X represents a carbon atom or a nitrogen atom), wherein the acyloxymethyl group of $R^2$ and $R^3$ is an acetyloxymethyl, propionyloxymethyl, butyryloxymethyl, isobutyryloxymethyl, valeryloxymethyl, isovaleryloxymethyl or pivaloyloxymethyl group and the acylthioethyl group of $R^2$ and $R^3$ is an acetylthioethyl, propionylthioethyl, butyrylthioethyl, isobutyrylthioethyl, valerythioethyl, isovalerythioethyl or pivaloylthioethyl group.

* * * * *